US012806171B2

(12) United States Patent
Agarwal et al.

(10) Patent No.: US 12,806,171 B2
(45) Date of Patent: Nov. 24, 2026

(54) TREATEMENT FOR CRYOPYRIN ASSOCIATED PERIODIC SYNDROMES (CAPS)

(71) Applicant: Zydus Lifesciences Limited, Ahmedabad (IN)

(72) Inventors: Sameer Agarwal, Ahmedabad (IN); Deven V Parmar, Ahmedabad (IN); Binu Philip, Ahmedabad (IN); Rajiv Sharma, Ahmedabad (IN); Mukut Jain, Ahmedabad (IN); Abhijit Chatterjee, Ahmedabad (IN)

(73) Assignee: ZYDUS LIFESCIENCES LIMITED, Ahmedabad (IN)

( * ) Notice: Subject to any disclaimer, the term of this patent is extended or adjusted under 35 U.S.C. 154(b) by 393 days.

(21) Appl. No.: 18/577,253

(22) PCT Filed: Jul. 8, 2022

(86) PCT No.: PCT/IB2022/056329
§ 371 (c)(1),
(2) Date: Jan. 6, 2024

(87) PCT Pub. No.: WO2023/281455
PCT Pub. Date: Jan. 12, 2023

(65) Prior Publication Data

US 2025/0041267 A1 Feb. 6, 2025

(30) Foreign Application Priority Data

Jul. 8, 2021 (IN) ............................ 202121030625

(51) Int. Cl.

| | |
|---|---|
| ***A61K 31/40*** | (2006.01) |
| ***A61K 45/06*** | (2006.01) |
| ***A61P 31/18*** | (2006.01) |
| ***A61P 37/06*** | (2006.01) |
| *C07D 233/60* | (2006.01) |
| *C07D 277/26* | (2006.01) |
| *C07D 307/64* | (2006.01) |
| *C07D 333/34* | (2006.01) |
| *C07D 471/04* | (2006.01) |

(52) U.S. Cl.
CPC .............. *A61K 31/40* (2013.01); *A61P 37/06* (2018.01)

(58) Field of Classification Search
CPC ......... A61K 31/40; A61K 45/06; A61P 37/06; A61P 31/18; C07D 207/08; C07D 233/60; C07D 277/26; C07D 307/64; C07D 471/04; C07D 333/34
See application file for complete search history.

(56) References Cited

FOREIGN PATENT DOCUMENTS

| | | | | | |
|---|---|---|---|---|---|
| WO | WO-2018225018 | A1 | * 12/2018 | ........... | C07D 305/08 |
| WO | 20200148619 | A1 | 7/2020 | | |

OTHER PUBLICATIONS

Laela M. Booshehri, et al., "CAPS and NLRP3," J Clin Immunol. (Apr. 2019); 39(3): pp. 277-286.
Rebecca C. Coll, et al., "A small molecule inhibitior of the NLRP3 inflammasome is a potential therapeutic for inflammatory diseases," Nat Med. (Mar. 2015) ; 21(3): pp. 248-255.
Charles A. Dinarello, et al., "Treating inflammation by blocking interleukin-1 in a broad spectrum of diseases," Nat Rev Drug Discov. (Aug. 2012) ; 11(8): pp. 633-652.
Tracey L. Freeman, et al., "Targeting the NRLP3 Inflammasome in severe COVID-19," Front. Immunol. 11:1518, Jun. 23, 2020, pp. 1-12.
Haitao Guo, et al., "Inflammasomes: Mechanism of action, role in disease, and therapeutics," Nature Medicine (Jun. 2015); 21(7), pp. 677-687.
E. Schuh, et al., "MCC950 blocks enhanced interleukin-1β production in patients with NLRP3 low penetrance variants," J Clin Immunol. (Apr. 2019); 27 pages.
Yang Yang, et al., "Recent advances in the mechanisms of NLRP3 inflammasome activation and its inhibitors," Cell Death and Disease (2019) 10:128; 11 pages.

* cited by examiner

*Primary Examiner* — Bruck Kifle
*Assistant Examiner* — Kevin S Martin
(74) *Attorney, Agent, or Firm* — Renner, Kenner, Greive, Bobak Taylor & Weber Co. LPA

(57) ABSTRACT

Present invention relates to development of compound of formula (I) for treatment of Cryopyrin Associated Periodic Syndromes (CAPS). Specifically, the present invention provides a NLRP3 inhibitors or its pharmaceutically acceptable salt for treatment of Cryopyrin Associated Periodic Syndromes (CAPS). Invention also relates to the pharmaceutical composition comprising compound of formula (I) or its pharmaceutically acceptable salts for treatment of Cryopyrin Associated Periodic Syndromes (CAPS).

5 Claims, No Drawings

TREATEMENT FOR CRYOPYRIN ASSOCIATED PERIODIC SYNDROMES (CAPS)

FIELD OF THE INVENTION

Present invention relates to development of compound of formula (I) for treatment of Cryopyrin Associated Periodic Syndromes (CAPS). Specifically, the present invention provides a NLRP3 inhibitors or its pharmaceutically acceptable salt for treatment of Cryopyrin Associated Periodic Syndromes (CAPS). Invention also relates to the pharmaceutical composition comprising compound of formula (I) or its pharmaceutically acceptable salts for treatment of Cryopyrin Associated Periodic Syndromes (CAPS).

BACKGROUND OF THE INVENTION

The nucleotide-binding oligomerization domain (NOD)-like receptor family, pyrin domain-containing 3 (NLRP3 or NALP3) inflammasome are a major source of mucosal interleukin (IL)-1β and the inflammasomes are mostly subject to activation by multiple aspects of inflammation-associated stress. NLRP3 is a cytosolic pattern recognition receptor (PRR) that senses exogenous and endogenous danger signals. The NLRP3 protein is made up of three domains: a leucine-rich repeat domain (LRR), a NOD containing a caspase activation and recruitment domain (CARD) (NACHT), and a pyrin domain (PYD). Upon activation, NLRP3 oligomerizes and triggers assembly of the adapter apoptosis-associated speck-like protein containing a CARD (ASC) via PYD-PYD interactions. ASC fibrils assemble into large structures, called ASC specks, and recruit pro-caspase-1, leading to its autoproteolytic activation. The activated caspase-1 is able to cleave pro-IL-1β and pro-IL-18 to generate the inflammatory cytokines IL-1β and IL-18 (Guo et al., 2015; Dinarello et al., 2012).

Involvement of the NLRP3 inflammasome in different kinds of diseases provides new avenues to design drugs targeting NLRP3 inflammasome. To date, clinical treatment of NLRP3-related diseases targets IL-1β with IL-1β antibodies or recombinant IL-1β receptor antagonist, such as canakinumab and anakinra, respectively. In addition, a few small-molecule compounds have shown anti-inflammatory effects on NLRP3 inflammasome activation in vitro, including MCC950, β-hydroxybutyrate (BHB), Bay 11-7082, dimethyl sulfoxide (DMSO), and type I interferon. However, most of these inhibitors are relatively nonspecific and have low efficacy. For inhibitors targeting IL-10, it should be noted that IL-1β secretion is not the only product of NLRP3 inflammasome activation; instead, other pro-inflammatory cytokines, including high-mobility group box 1 (HMGB1) and IL-18 may participate in the pathogenesis of these diseases. Moreover, IL-1β can be produced by inflammasome-independent pathways or other inflammasomes. Therefore, inhibitors targeting IL-1β may lead to unintended immunosuppressive effects besides preventing NLRP3 inflammasome activation itself. Pharmacological inhibitors specific to NLRP3 inflammasome may be the best choice for treatment of NLRP3-related diseases. (Yang et al., 2019).

Cryopyrin-associated periodic syndromes (CAPs) are a rare family of heterogeneous autoinflammatory diseases characterized by IL-1β-mediated systemic inflammation and clinical symptoms involving skin, joints, central nervous system and eyes. CAPS is associated with an activating mutation in NLRP3, of which approximately 200 mutations have been defined. While some mutations have been classed as benign and present with no deleterious clinical phenotype, approximately 100 of the reported mutations result in a chronic pro-inflammatory presentation. CAPS is categorized into three clinical subgroups of increasing severity: familial cold autoinflammatory syndrome (FCAS), Muckle-Wells syndrome (MWS), and neonatal-onset multisystem inflammatory disease (NOMID), also called chronic infantile neurologic cutaneous and articular syndrome or CINCA) (Booshehri et al., 2019). Mice that harbour the mutant forms of NLRP3 that occur in CAPS die in the neonatal period and have increased concentrations of circulating IL-1β and IL-18 (Coll et al. 2015). Previously demonstrated that MCC950 inhibited NLRP3 activation in a mouse model of MWS. Peripheral blood mononuclear cells (PBMC) from patients with low penetrance NLRP3 variants (Q703K and V198M) have been shown to display enhanced IL-1β levels following inflammasome activation compared to healthy controls. Furthermore, release of IL-1β has been shown to be NLRP3-dependent as it was blocked by MCC950 (Schuh et al., 2019). The IL-1β receptor antagonist anakinra is conventionally used to control the symptoms of the syndrome, but patients relapse when treatment is withdrawn.

There are various agents in various stages of Phase 1 and Phase II development that target the NLRP3 inflammasome. (Freeman et al., 2020). Agents like MCC950, CY-09, OLT1177, Tranilast, Oridonin, NT-0167 displayed the good therapeutic properties, as they directly target NLRP3 itself, but not other components (NEK7, ASC, caspase-1, or IL-1β) up-/downstream of NLRP3 inflammasome activation. Furthermore, these inhibitors are being used in clinical practice are being investigated at phase II clinical trials having shown relatively high safety (Yang et al., 2019).

NLRP3 in innate immune cells are activated by Pathogen Associated Molecular Patterns and Death Associated Molecular Patterns. The resultant NLRP3 inflammasome activates Caspase-1 and in-turn cleave and releases IL-1b and IL-18. NLRP3 inflammasome inhibitors have potential to negate IL-1 mediated disease pathologies including CAPS.

All current therapies are limited to injectable biologics that often have limited central nervous system (CNS) penetration, which is particularly important in NOMID patients with severe CNS disease. Therefore, there remains an unmet clinical need for more targeted, and preferably small molecule, compounds as an alternative to IL-1 targeted biologics.

Embodiments of the Invention

In an embodiment, the present invention provides a therapeutic compound of formula (I) or its pharmaceutically acceptable salts suitable for the treatment and prevention of Cryopyrin Associated Periodic Syndromes (CAPS).

Formula (I)

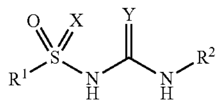

In another embodiment, the present invention provides pharmaceutical composition comprising compound of formula (I) or its pharmaceutically acceptable salts and pharmaceutically acceptable excipients for the treatment and prevention of Cryopyrin Associated Periodic Syndromes (CAPS).

In yet another embodiment, the present invention provides the administration of therapeutic compound of formula (I) and their pharmaceutically acceptable salts alone or in combination with suitable for the treatment and prevention of Cryopyrin Associated Periodic Syndromes (CAPS).

In a further embodiment, the present invention provides use of compound of formula (I) or its pharmaceutically acceptable salts for the treatment of Cryopyrin Associated Periodic Syndromes (CAPS).

In another embodiment, the present invention provides a method of treating Cryopyrin Associated Periodic Syndromes (CAPS) using pharmaceutical composition of compound of formula (I) or its pharmaceutically acceptable salts.

The above and other embodiments of the present invention are disclosed further hereinafter.

SUMMARY OF THE INVENTION

The present invention provides a therapeutic compound of formula (I) or its pharmaceutically acceptable salts for the prevention and treatment of Cryopyrin Associated Periodic Syndromes (CAPS) and related diseases. Present invention also relates to pharmaceutical composition comprising compound of formula (I) or pharmaceutically acceptable excipients useful for the treatment of Cryopyrin Associated Periodic Syndromes (CAPS).

DETAIL DESCRIPTION OF THE INVENTION

Definition

The terms 'treatment' or 'treat' refer to slowing, stopping, or delaying the progression of the disease or clinical symptoms in a patient, as evidenced by a decrease or elimination of a clinical or diagnostic symptom of the disease, disorder or condition.

The term 'subject' refer to a mammals.

The term 'effective amount' in the context of the administration of the amount of the drug substance sufficient to have the desired effect.

"Patient" includes both human and animals. "Mammal" means humans and other mammalian animals.

The term "preventing" refers to barring a subject from acquiring a disorder or disease in the first place.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As used herein "treating" includes achieving, partially or substantially, one or more of the following results: partially or totally reducing the extent of the disease, disorder or syndrome. Delaying, inhibiting or preventing the progression of the disease, disorder or syndrome includes for example, delaying, inhibiting or preventing the progression of. Cryopyrin Associated Periodic Syndromes (CAPS).

The present invention describes a method of treating a subject suffering from Cryopyrin Associated Periodic Syndromes (CAPS).

In an embodiment the present invention provides a compound of formula (I) or its pharmaceutically acceptable salts suitable for the treatment of Cryopyrin Associated Periodic Syndromes (CAPS).

In a further embodiment the present invention provides use of the compound of formula (I) or their suitable pharmaceutical compositions for the treatment of Cryopyrin Associated Periodic Syndromes (CAPS).

The method comprises administering to a subject an effective amount of a compound according to Formula (I), Formula (I)

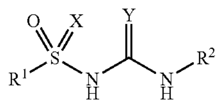

their tautomeric forms, their stereoisomers; their enantiomers; their metabolites; their deuterium analogs; their pharmaceutically acceptable salts; and pharmaceutical compositions containing them or their mixtures thereof, wherein X is O, NH, or N—$R^3$ wherein $R^3$ at each occurrence independently represents hydrogen, hydroxyl, halogen, nitro, cyano, haloalkyl, optionally substituted groups selected from ($C_1$-$C_{10}$)alkyl, ($C_1$-$C_{10}$)alkoxy, ($C_3$-$C_{10}$)cycloalkyl, ($C_2$-$C_{10}$)alkenyl, ($C_2$-$C_{10}$)alkynyl, $SO_2$($C_1$-$C_6$)alkyl, thiol, thioalkyl, thio-alkoxy, SO($C_1$-$C_6$)alkyl, benzyl, aryl, heteroaryl, heterocyclyl;

Y is O, S;

$R^1$ at each occurrence independently represents hydrogen, halogen, haloalkyl, cyano, optionally substituted groups selected from ($C_1$-$C_6$)alkyl, ($C_1$-$C_6$)haloalkyl, ($C_2$-$C_6$)alkenyl, ($C_2$-$C_6$)alkynyl, ($C_1$-$C_6$)alkoxy, ($C_3$-$C_7$)cycloalkyl, ($C_1$-$C_6$)alkyl$SO_2$($C_1$-$C_6$)alkyl, ($C_1$-$C_6$)alkylN($C_1$-$C_6$)alkyl, ($C_1$-$C_6$)alkylN($C_3$-$C_7$)cycloalkyl, aryl, heteroaryl, heterocyclyl, benzyl, tert-butyloxycarbonyl, NH($C_1$-$C_6$)alkyl, N(($C_1$-$C_6$)alkyl)$_2$, NH($C_2$-$C_6$)alkenyl, N(($C_2$-$C_6$)alkenyl)$_2$, —N-heterocyclyl, N($C_1$-$C_6$)alkyl-heterocyclyl, NR'R", thiol, mercaptoalkyl, $SO_2$($C_1$-$C_6$)alkyl, $SO_2$($C_3$-$C_7$)cycloalkyl, $SO_2$-aryl, $SO_2$-heterocyclyl, ($C_1$-$C_6$)thioalkyl, ($C_1$-$C_6$)thioalkoxy, ($C_1$-$C_6$)alkyl$SO_2NH_2$, —$CONH_2$, —CO($C_1$-$C_6$)alkyl, —CO($C_1$-$C_6$)haloalkyl, —CO-aryl, —CO-heteroaryl, —CO-heterocyclyl, 4- to 7-membered heterocyclic ring, 7- to 14-membered bicyclic heterocyclic ring system, bridged or spiro ring system having optionally one or more than one heteroatoms;

In an embodiment $R^1$ represents:

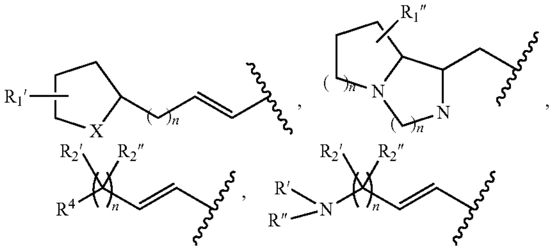

n, is independently selected from integer 0-3;

each of R', R", $R_1$', $R_1$", $R_2$' and $R_2$" at each occurrence independently represents hydrogen, halogen, haloalkyl, cyano, optionally substituted groups selected from ($C_1$-$C_6$)alkyl, ($C_1$-$C_6$)haloalkyl, ($C_2$-$C_6$)alkenyl, ($C_2$-$C_6$)alkynyl, ($C_1$-$C_6$)alkoxy, ($C_3$-$C_7$)cycloalkyl, ($C_1$-$C_6$)alkyl$SO_2$($C_1$-$C_6$)alkyl, ($C_1$-$C_6$)alkylN($C_1$-$C_6$)alkyl, ($C_1$-$C_6$)alkylN($C_3$-$C_7$)cycloalkyl, aryl, heteroaryl, heterocyclyl, benzyl, tert-butyloxycarbonyl, thiol, mercaptoalkyl, $SO_2(C_1\text{-}C_6)$alkyl, $SO_2(C_3\text{-}C_7)$cycloalkyl, $SO_2$-aryl, $SO_2$-heterocyclyl, $(C_1\text{-}C_6)$thioalkyl, $(C_1\text{-}C_6)$ thioalkoxy, $(C_1\text{-}C_6)$alkyl$SO_2NH_2$, —$CONH_2$, —CO $(C_1\text{-}C_6)$alkyl, —CO$(C_1\text{-}C_6)$haloalkyl, —CO-aryl, —CO-heteroaryl, —CO-heterocyclyl, 4- to 7-membered heterocyclic ring, 7- to 14-membered bicyclic heterocyclic ring system, bridged or spiro ring system having optionally one or more than one heteroatoms; In an embodiment R' and R" optionally forms 4- to 7-membered heterocyclic ring system.

$R^2$ is selected from the following ring system

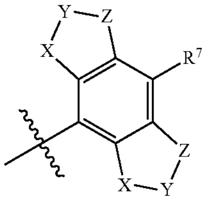

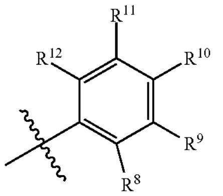

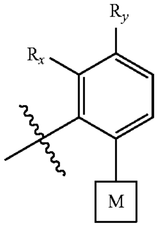

wherein X, Y, Z at each occurrence independently represents C, N, S, $SO_2$, and O, which may be optionally substituted;

each of $R^7$, $R^8$, $R^9$, $R^{10}$, $R^{11}$ and $R^{12}$ at each occurrence are independently selected from hydrogen, halogen, cyano, amide, sulphonamide, acyl, hydroxyl, optionally substituted groups selected from $(C_1\text{-}C_6)$alkyl, $(C_1\text{-}C_6)$haloalkyl, $(C_3\text{-}C_6)$cycloalkyl, $(C_1\text{-}C_6)$alkoxy, benzyl, aryl, heteroaryl, heterocyclyl; In one embodiment each of $R^8$ and $R^9$, $R^9$ and $R^{10}$, $R^{10}$ and $R^{11}$ and $R^{11}$ and $R^{12}$ wherever possible, together may form a 4 to 7 membered saturated or partially saturated ring containing from 0-2 additional heteroatoms selected from the group consisting of N, O, and $S(O)_p$; p=1-2.

$R_x$ and $R_y$ at each occurrence are independently selected from hydrogen, halogen, optionally substituted groups selected from $(C_1\text{-}C_6)$alkyl; Alternatively $R_x$ and $R_y$ together may form a 4- to 7-membered heterocyclic ring system;

'M' is selected from aryl, heteroaryl, heterocyclyl;

When any of above defined group is substituted the substitutions on them may be selected from those described above or may be selected from hydrogen, hydroxy, cyano, halo, haloalkyl, haloalkyloxy, alkylthio, optionally substituted group selected from $(C_1\text{-}C_6)$alkyl, $(C_2\text{-}C_6)$alkenyl, $(C_2\text{-}C_6)$alkynyl, $(C_3\text{-}C_{10})$cycloalkyl, $C_1\text{-}C_6$ alkoxy, aryl, heterocyclyl, heteroaryl, —$COR_{11}$, —$CSR_{11}$, $C(O)OR_{11}$, C(O)—$R_{11}$, —C(O)—$NR_{11}R_{12}$, —C(S)—$NR_{11}R_{12}$, —$SO_2R_{11}$ group, wherein each of, $R_{11}$ and $R_{12}$ is independently selected from hydrogen, optionally substituted group selected from $(C_1\text{-}C_6)$alkyl, $(C_2\text{-}C_6)$alkenyl, $(C_2\text{-}C_6)$alkynyl, $(C_3\text{-}C_7)$cycloalkyl, aryl, heteroaryl, heterocyclyl groups;

In a preferred embodiment, the groups, radicals described above may be selected from:

"Alkyl", as well as other groups having the prefix "alk", such as alkoxy and alkanoyl, means a carbon chain which may further be substituted with an oxygen atom as is well understood by a skilled artisan, which may further be either linear or branched, and combinations thereof, unless the carbon chain is defined otherwise. Examples of alkyl group include but not limited to methyl, ethyl, propyl, isopropyl, butyl, sec-butyl, tert. -butyl, pentyl, hexyl etc. Where the specified number of carbon atoms permits e.g. from $C_{3\text{-}10}$, the term alkyl also includes cycloalkyl groups, and combinations of linear or branched alkyl chains combined with cycloalkyl structures. When no number of carbon atoms is specified, $C_{1\text{-}6}$ is intended. Substituted alkyl includes alkyl substituted with one or more moieties selected from the group consisting of halo {e.g., CI, F, Br, and I); halogenated alkyl {e.g., $CF_3$, 2-Br-ethyl, $CH_2F$, $CH_2CI$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate as well as those described under the definition of 'Optionally substituted'.

"Alkenyl" means carbon chains which contain at least one carbon-carbon double bond, and which may be linear or branched or combinations thereof, unless the carbon chain is defined otherwise. Examples of alkenyl include but not limited to vinyl, allyl, isopropenyl, hexenyl, pentenyl, heptenyl, 1-propenyl, 2-butenyl, 2-methyl-2-butenyl etc. Where the specified number of carbon atoms permits, e.g., from $C_{5\text{-}10}$, the term alkenyl also includes cycloalkenyl groups and combinations of linear, branched and cyclic structures. When no number of carbon atoms is specified, $C_{2\text{-}6}$) is intended.

"Alkynyl" means carbon chains which contain at least one carbon-carbon triple bond, and which may be linear or branched or combinations thereof. Examples of alkynyl include ethynyl, propargyl, 3-methyl-1-pentynyl etc. When no number of carbon atoms is specified, is intended.

the "thioalkyl" group used either alone or in combination with other radicals, denotes an alkyl group, as defined above, attached to a group of formula —SR', (sulfur and its oxidized forms) where R' represents hydrogen, alkyl or aryl group, e.g. thiomethyl, methylthiomethyl, phenylthiomethyl and the like, which may be optionally substituted.

As used herein, "carbocycle" or "carbocyclic residue" is intended to mean any stable monocyclic or bicyclic or tricyclic ring, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). In a broader perspective, the term carbocycle is intended to include, wherever applicable, the groups representing cycloalkyl, phenyl and other saturated, partially saturated or aromatic residues;

The terms "cycloalkyl" and "cycloalkenyl" refers to optionally substituted, saturated and unsaturated mono-cyclic, bicyclic or tricyclic carbon groups. Where appropriate, the cycloalkyl or cycloalkenyl group may have a specified number of carbon atoms, for example, $C_3\text{-}C_6$ cycloalkyl or cycloalkenyl includes within its scope a carbocyclic group having 3, 4, 5 or 6 carbon atoms. Examples of such substituents may be selected from the group consisting of cyclopropyl, cyclobutyl, cyclopentyl, cyclopentenyl, cyclohexyl, cyclohexenyl, cyclohexadienyl and the like. Substituted cycloalkyl or cycloalkenyl includes substitutions with one or more moieties selected from the group consisting of halo (e.g., CI, F, Br, and I); halogenated alkyl (e.g., $CF_3$, 2-Br-ethyl, $CH_2F$, $CH_2CI$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate as well as those described under the definition of 'Optionally substituted'.

The "alkoxy" refers to the straight or branched chain alkoxides of the number of carbon atoms specified.

"Aryl" means a mono- or polycyclic aromatic ring system containing carbon ring atoms. The preferred aryls are monocyclic or bicyclic 6-10 membered aromatic ring systems. Phenyl and naphthyl are preferred aryls.

"Heterocyclyl" means a saturated, partially saturated or unsaturated aromatic or non-aromatic mono, bi or tricyclic radicals, containing one or more heteroatoms selected from nitrogen, sulfur and oxygen, further optionally including the oxidized forms of sulfur, namely SO & $SO_2$ Heterocyclyl systems may be attached to another moiety via any number of carbon atoms or heteroatoms of the radical and may be both saturated and unsaturated. Examples of heterocycles include tetrahydrofuran (THF), dihydrofuran, 1,4-dioxane, morpholine, 1,4-dithiane, piperazine, piperidine, 1,3-dioxolane, imidazoline, imidazolidine, pyrrolidine, pyrroline, tetrahydropyran, dihydropyran, oxathiolane, dithiolane, 1,3-dioxane, 1,3-dithiane, oxathiane, thiomorpholine, etc. The term "heterocycloalkyl" refers to a heterocyclic group as defined above connected to an alkyl group as defined above;

"Heteroaryl" means an aromatic or partially aromatic heterocycle that contains at least one ring heteroatom selected from O, S and N. Heteroaryls thus include heteroaryls fused to other kinds of rings, such as aryls, cycloalkyls, and heterocycles that are not aromatic. Examples of heteroaryl groups include; pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzthiazolyl, benzothiadiazolyl, dihydrobenzofuranyl, indolinyl, pyridazinyl, indazolyl, isoindolyl, dihydrobenzothienyl, indolinyl, pyridazinyl, indazolyl, isoindolyl, dihydrobenzothienyl, indolizinyl, cinnolinyl, phthalazinyl, quinazolinyl, napthyridinyl, carbazolyl, benzodioxolyl, quinoxalinyl, purinyl, furazanyl, isobenzylfuranyl, benzimidazolyl, benzofuranyt, benzothienyl, quinolyl, indolyl, isoquinolyl, dibenzofuranyl etc. For heterocyclyl; and heteroaryl groups, rings and ring systems containing from 3-15 carbon atoms are included, forming 1-3 rings.

The term "haloalkyl" means an alkyl structure in which at least one hydrogen is replaced with a halogen atom. In certain embodiments in which two or more hydrogen atoms are replaced with halogen atoms, the halogen atoms are all the same as one another.

the "haloalkoxy" group is selected from suitable haloalkyl, as defined above, directly attached to an oxygen atom, more preferably groups selected from fluoromethoxy, chloromethoxy, fluoroethoxy, chloroethoxy and the like;

In certain other embodiment in which two or more hydrogen atoms are replaced with halogen atoms, the halogen atoms are not all the same as one another.

"Aryloxyalkyl" means an alkyl radical substituted with aryloxy group as defined herein.

"Aryloxyaryl" means an aryl radical substituted with aryloxy group as defined herein.

"Aryloxyheteroaryl" means a heteroaryl radical substituted with aryloxy group as defined herein.

"Halo/Halogen" refers to fluorine, chlorine, bromine, iodine. Chlorine and fluorine are generally preferred.

Suitable groups and substituents on the groups may be selected from those described anywhere in the specification.

The term "substituted," as used herein, means that any one or more hydrogen on the designated atom is replaced with a selection from the indicated group, provided that the designated atom's normal valency is not exceeded, and that the substitution results in a stable compound. The term "substituted," as used herein, means that any one or more hydrogens on the designated atom is replaced with a selection from the indicated group, provided that the designated atom's normal valency is not exceeded, and that the substitution results in a stable compound.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. Such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromie, hydrochloric, hydroiodide, hydroxymaleic, hydroxynaphthoic, isethionic, lactic, lactobionic, -lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The term 'optional' or 'optionally' means that the subsequent described event or circumstance may or may not occur, and the description includes instances where the event or circumstance occur and instances in which it does not. For example, optionally substituted alkyl' means either 'alkyl' or 'substituted alkyl'. Further an optionally substituted group includes an unsubstituted group.

Unless otherwise stated in the specification, structures depicted herein are also meant to include compounds which differ only in the presence of one or more isotopically enriched atoms.

Particularly useful compounds may be selected from but not limited to the following:

N'-cyano-N-((1,2,3,5,6,7-hexahydro-s-indacen-4-yl)carbamoyl)-5-(2-hydroxypropan-2-yl)thiophene-2-sulfonimidamide;

N'-cyano-4-fluoro-N-((1,2,3,5,6,7-hexahydro-s-indacen-4-yl)carbamoyl)-3-(2-hydroxypropan-2-yl)benzenesulfonimidamide;

N'-cyano-N-((1,2,3,5,6,7-hexahydro-s-indacen-4-yl)carbamoyl)-4-(2-hydroxypropan-2-yl)furan-2-sulfonimidamide;

(E)-N-((1,2,3,5,6,7-hexahydro-s-indacen-4-yl)carbamoyl)-2-(thiazol-2-yl)ethenesulfonamide;

(E)-2-(1-ethyl-1H-imidazol-2-yl)-N-((1,2,3,5,6,7-hexahydro-s-indacen-4-yl)carbamoyl)ethenesulfonamide;

(E)-2-(1-ethyl-4-methyl-1H-imidazol-2-yl)-N-((1,2,3,5,6,7-hexahydro-s-indacen-4-yl)carbamoyl)ethenesulfonamide;

(R,E)-2-(1-ethylpyrrolidin-2-yl)-N-((1,2,3,5,6,7-hexahydro-s-indacen-4-yl)carbamoyl)-ethanesulfonamide;

(R,E)-N-((1,2,3,5,6,7-hexahydro-s-indacen-4-yl)carbamoyl)-2-(pyrrolidin-2-yl)ethene-1-sulfonamide;

(R,E)-N-((1,2,3,5,6,7-hexahydro-s-indacen-4-yl)carbamoyl)-2-(1-methylpyrrolidin-2-yl)ethene-1-sulfonamide;

(S,E)-2-(1-ethylpyrrolidin-2-yl)-N-((1,2,3,5,6,7-hexahydro-s-indacen-4-yl)carbamoyl)-ethanesulfonamide;

(R,E)-2-(1,2-dimethylpyrrolidin-2-yl)-N-((1,2,3,5,6,7-hexahydro-s-indacen-4-yl)carbamoyl)ethene-1-sulfonamide;

(S,E)-2-(1,2-dimethylpyrrolidin-2-yl)-N-((1,2,3,5,6,7-hexahydro-s-indacen-4-yl)carbamoyl)ethene-1-sulfonamide;

sodium(S,E)-((2-(1,2-dimethylpyrrolidin-2-yl)vinyl)sulfonyl)((1,2,3,5,6,7-hexahydro-s-indacen-4-yl)carbamoyl)amide;

potassium (R,E)-((2-(1,2-dimethylpyrrolidin-2-yl)vinyl)sulfonyl)((1,2,3,5,6,7-hexahydro-s-indacen-4-yl)carbamoyl)amide;

Sodium(R,E)-((2-(1,2-dimethylpyrrolidin-2-yl)vinyl)sulfonyl)((1,2,3,5,6,7-hexahydro-s-indacen-4-yl)carbamoyl)amide;

(E)-N'-cyano-2-((S)-1,2-dimethylpyrrolidin-2-yl)-N-((1,2,3,5,6,7-hexahydro-s-indacen-4-yl)carbamoyl)ethene-1-sulfonimidamide;

(E)-N'-cyano-N-((1,2,3,5,6,7-hexahydro-s-indacen-4-yl)carbamoyl)-2-((R)-1-methylpyrrolidin-2-yl)ethene-1-sulfonimidamide;

(E)-N'-cyano-2-((R)-1,2-dimethylpyrrolidin-2-yl)-N-((1,2,3,5,6,7-hexahydro-s-indacen-4-yl)carbamoyl)ethene-1-sulfonimidamide;

N-((1,2,3,5,6,7-hexahydro-s-indacen-4-yl)carbamoyl)-1-((1S,8aR)-3,3,8a-trimethyloctahydropyrrolo[1,2-a]pyrazin-1-yl)methanesulfonamide;

N-((1,2,3,5,6,7-hexahydro-s-indacen-4-yl)carbamoyl)-1-((4S,8aS)-2,3,3,8a-tetramethyloctahydropyrrolo[1,2-a]pyrazin-4-yl)methanesulfonamide;

(E)-3-(dimethylamino)-N-((1,2,3,5,6,7-hexahydro-s-indacen-4-yl)carbamoyl)prop-1-ene-1-sulfonamide;

sodium (E)-((3-(dimethylamino)-3-methylbut-1-en-1-yl)sulfonyl)((1,2,3,5,6,7-hexahydro-s-indacen-4-yl)carbamoyl)amide;

(S,E)-N-((1,2,3,5,6,7-hexahydro-s-indacen-4-yl)carbamoyl)-2-(2-methyl-1-(methyl-d)pyrrolidin-2-yl)ethene-1-sulfonamide;

(R,E)-N-((1,2,3,5,6,7-hexahydro-s-indacen-4-yl)carbamoyl)-2-(2-methyl-1-(methyl-d)pyrrolidin-2-yl)ethene-1-sulfonamide;

(R,E)-N-((1,2,3,5,6,7-hexahydro-s-indacen-4-yl)carbamoyl)-2-(1-(methyl-d)pyrrolidin-2-yl)ethene-1-sulfonamide;

or pharmaceutically acceptable salts of any of the compounds above.

Following is a list of abbreviations used in the description of the preparation of the compounds of the present invention:

μg: microgram
$^1$H NMR: Proton nuclear magnetic resonance
bs: broad singlet
$CDCl_3$: Deuterated chloroform
$CHCl_3$: Chloroform
d: doublet
DAMP: damage-associated molecular pattern;
DBU: 1,8-Diazabicyclo(5.4.0)undec-7-ene
DCM: Dichloromethane
dd: doublet of doublet
DMAC: N,N-(Dimethylacetamide)
DMAP: 4-(Dimethylamino) pyridine
DMF: N,N-Dimethyl formamide
DMSO: Dimethyl sulfoxide
dt: doublet of triplet
EDTA: Ethylenediaminetertraacetic acid
EtOAc: Ethyl acetate
EtOH: Ethanol
HCl(g): Hydrogen chloride (gas)
IL1β: Interleukin 1 beta
$K_2CO_3$: Potassium carbonate
m: multiplet
MeOH: Methanol
mmol: millimoles
MS: Mass spectrum
$N_2$: Nitrogen
$Na_2CO_3$: Sodium carbonate
ng: nanogram
NIS: Niodosuccinimide
PAMP: pathogen-associated molecular pattern;
PMA: Phorbol 12-myristate 13-acetate
$POCl_3$: Phosphorylchloride
RM: reaction mixture
r.t., RT: room temperature
s: singlet
t: Triplet
td: triplet of doublet
THF: Tetrahydrofuran
TLC: Thin layer chromatography
TLR: Toll-like receptor.
TNF a: Tumor necrosis factor alpha
WT: Wild type
A441V: Alanine 441 position to Valine
E692K: Glutamic Acid 692 to Lysine
A439V: Alanine 439 position to Valine
A441V: Alanine 441 position to Valine
A439V: Alanine 439 position to Valine The term "pharmaceutical composition" refers to a mixture of an NLRP3 antagonist or other compound described herein with other chemical components (referred to collectively herein as"excipients"), such as carriers, stabilizers, diluents, dispersing agents, suspending agents, and/or thickening agents. The pharmaceutical composition facilitates administration of the NLRP3 antagonist or other compound to an organism. Multiple techniques of administering a compound exist in the art including, but not limited to rectal, oral, and intravenous, aerosol, and parenteral, ophthalmic, pulmonary, and topical administration.

In an embodiment, the present invention provides effective amount of compound of formula (I) or its pharmaceutically acceptable salts may be selected from 1 mg to 500 mg; preferably 1 mg to 250 mg and more preferably 1 mg to 150 mg for the treatment and prevention of Cryopyrin Associated Periodic Syndromes (CAPS).

In certain other embodiments, the compound is administered orally in an amount to provide compound of formula (I) or a pharmaceutically acceptable salt thereof in the range of about 1 mg to about 50 mg on each day the compound is administered to the subject. In certain embodiments, the compound is administered orally in an amount to provide compound of formula (I) or a pharmaceutically acceptable salt thereof in the range of about 1 mg to about 100 mg on each day the compound is administered to the subject. In certain embodiments, the compound is administered orally in an amount to provide compound of formula (I) or a pharmaceutically acceptable salt thereof in the range of about 1 mg to about 150 mg on each day the compound is administered to the subject. In certain embodiments, the compound is administered orally in an amount to provide compound of formula (I) or a pharmaceutically acceptable salt thereof in the range of about 1 mg to about 200 mg on each day the compound is administered to the subject. In certain embodiments, the compound is administered orally in an amount to provide compound of formula (I) or a pharmaceutically acceptable salt thereof in the range of about 1 mg to about 250 mg on each day the compound is administered to the subject. In certain embodiments, the compound is administered orally in an amount to provide compound of formula (I) or a pharmaceutically acceptable salt thereof in the range of about 1 mg to about 300 mg on each day the compound is administered to the subject. In certain embodiments, the compound is administered orally in an amount to provide compound of formula (I) or a pharmaceutically acceptable salt thereof in the range of about 1 mg to about 350 mg on each day the compound is administered to the subject. In certain embodiments, the compound is administered orally in an amount to provide compound of formula (I) or a pharmaceutically acceptable salt thereof in the range of about 1 mg to about 400 mg on each day the compound is administered to the subject. In certain embodiments, the compound is administered orally in an amount to provide compound of formula (I) or a pharmaceutically acceptable salt thereof in the range of about 1 mg to about 450 mg on each day the compound is administered to the subject. In certain embodiments, the compound is administered orally in an amount to provide compound of formula (I) or a pharmaceutically acceptable salt thereof in the range of about 1 mg to about 500 mg on each day the compound is administered to the subject.

In an embodiment, the present invention provides effective amount of compound of formula (I) or its pharmaceutically acceptable salt may be administered by oral, topical, parenteral, intravenous or intramuscular route of administration. In a preferred embodiment, the present invention provides effective amount of formula (I) or its pharmaceutically acceptable salts is administered by oral route of administration.

The compound of formula (I) or its pharmaceutically acceptable salts may be provided to the subject daily, weekly, as prescribed by physician to the person in need thereof.

In another embodiment, the present invention provides a method of treating a subject suffering from Cryopyrin Associated Periodic Syndromes (CAPS), which comprises treatment of a patient in need of such therapy, with compound of formula (I) or its pharmaceutically acceptable salts or suitable pharmaceutical compositions containing them.

In an embodiment, the present invention provides the combination of compound of formula (I) and their pharmaceutically acceptable salts with other suitable agents as therapeutic agent for the treatment of Cryopyrin Associated Periodic Syndromes (CAPS).

In an embodiment, the additional therapeutic agent used is selected from Inhibitors of interleukin-1β (e.g. Rilonacept, Canakinumab, and Anakinra); immune-suppressants (e.g., Methotrexate, Mercaptopurine, Cyclophosphamide), metabolic disorders drugs, glucocorticoids, non-steroidal anti-inflammatory drugs, Gasdermin D inhibitors (e.g., Necrosulfonamide); Cox-2 specific inhibitors, TNF-α binding proteins (e.g., Infliximab, Etanercept), Interferon-13, Interferon, Interleukin-2, antihistamines, beta-agonist, BTK inhibitors, anticolinergics, anti-cancer agents; anti-viral drugs, for example: Remdesivir, Lopinavir/Ritonavir, Favipiravir, Molnupiravir, Tamiflu; anti-malarial agents, for example: Choloroquinone, Hydroxyl Chloroquinone; or their suitable pharmaceutically acceptable salts. Further examples for use in combination with Non-Alcoholic Steato-Hepatitis (NASH) and fibrosis drugs; anticancer; antibiotics, for example Azithromycin; hormones, Aromatase inhibitors, Colchicine, Anticoagulants, antibodies, cytokines, anti-IL6 drugs; Antiparasitics; vaccines; Interferons; drug conjugates; Drugs originally developed for SARS (ACE2 protein decoy); Intravenous vitamin C; inhibitors of mitogen-activated protein kinase signaling (ex: BAY 43-9006); Syk inhibitors; mTOR inhibitors; antibodies (Rituxan); and BCR/ABL antagonist.

In yet another embodiment, compound of formula (I) is provided in the form of pharmaceutical composition.

In an embodiment, present invention provides a pharmaceutical composition comprising compound of formula (I) or its pharmaceutically acceptable salts for treatment of Cryopyrin Associated Periodic Syndromes (CAPS) wherein compound of formula (I) is Formula (I)

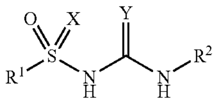

In an embodiment, the present invention provides pharmaceutical composition comprising compound of formula (I) and suitable pharmaceutically acceptable excipients for the treatment of Cryopyrin Associated Periodic Syndromes (CAPS).

The pharmaceutically acceptable excipients may be selected at least one from diluents, carriers, binders, disintegrating agents, lubricating agents, surface active agents and the like.

In an embodiment, the present invention provides a pharmaceutical composition comprising compound of formula (I) or its pharmaceutically acceptable salts wherein effective amount of compound of formula (I) or its pharmaceutically acceptable salt may be selected from 1 mg to 500 mg; preferably 1 mg to 250 mg and more preferably 1 mg to 150 mg for the treatment of Cryopyrin Associated Periodic Syndromes (CAPS).

In an embodiment, the present invention provides pharmaceutical composition comprising compound of formula (I) or its pharmaceutically acceptable salt may be administered by oral, topical, parenteral, intravenous or intramuscular route of administration. In a preferred embodiment, the pharmaceutical composition may be administered by oral route of administration.

In another embodiment of the present invention provides a process for the preparation of a stable pharmaceutical composition of compounds of formula (1).

The stable pharmaceutical composition may be made by dry mixing, wet granulation or dry granulation methods by techniques known to persons skilled in the art. Thus, for example, In wet granulation process, the drug is mixed with one or more pharmaceutical excipients and granulated with suitable binding solution as described earlier, to form wet granules, the wet granules are dried and optionally sieved. The dried granules are mixed with one or more suitable excipients from those described elsewhere and then compressed into tablets or filled into capsules.

In dry mixing process, the drug is mixed with all the pharmaceutical excipients required. Theblend is mixed with one or more suitable excipients from those described elsewhere and then final blend is either compressed into tablets or filled in capsules.

In dry granulation process, the drug is mixed with one or more pharmaceutical excipients and compressed into slugs and these slugs are passed through required sieve. The sieved granules are mixed with one or more suitable excipients from those described elsewhere and then compressed into tablets or filled into capsules.

One or more solvents or vehicle used in the formulation are selected from water, acetone, chloroform, dichloromethane, ethyl alcohol, ethyl acetate, methyl alcohol, isopropyl alcohol and combinations thereof and other such materials known to those of ordinary skill in the art.

In yet another embodiment, the present invention provides the administration of compound of formula (I) and their pharmaceutically acceptable salts alone or in combination with other suitable agents as therapeutic agent for the treatment of Cryopyrin Associated Periodic Syndromes (CAPS).

In an embodiment, the additional therapeutic agent used is selected from Inhibitors of interleukin-1β (e.g. Rilonacept, Canakinumab, and Anakinra); immune-suppressants (e.g., Methotrexate, Mercaptopurine, Cyclophosphamide), metabolic disorders drugs, glucocorticoids, non-steroidal anti-inflammatory drugs, Gasdermin D inhibitors (e.g., Necrosulfonamide); Cox-2 specific inhibitors, TNF-α binding proteins (e.g., Infliximab, Etanercept), Interferon-13, Interferon, Interleukin-2, antihistamines, beta-agonist, BTK inhibitors, anticolinergics, anti-cancer agents; anti-viral drugs, for example: Remdesivir, Lopinavir/Ritonavir, Favipiravir, Molnupiravir, Tamiflu; anti-malarial agents, for example: Choloroquinone, Hydroxyl Chloroquinone; or their suitable pharmaceutically acceptable salts. Further examples for use in combination with Non-Alcoholic Steato-Hepatitis (NASH) and fibrosis drugs; anticancer; antibiotics, for example Azithromycin; hormones, Aromatase inhibitors, Colchicine, Anticoagulants, antibodies, cytokines, anti-IL6 drugs; Antiparasitics; vaccines; Interferons; drug conjugates; Drugs originally developed for SARS (ACE2 protein decoy); Intravenous vitamin C; inhibitors of mitogen-activated protein kinase signaling (ex: BAY 43-9006); Syk inhibitors; mTOR inhibitors; antibodies (Rituxan); and BCR/ABL antagonist.

Compositions of the invention are also used in combination with other active ingredients. For the treatment of Arenaviridae virus infections, preferably, the other active therapeutic agent is active against Arenaviridae virus infections, particularly Lassa virus and Junin virus infections. Non-limiting examples of these other active therapeutic agents are Ribavirin, Favipiravir (also known as T-705 or Avigan), T-705 monophosphate, T-705 diphosphate, T-705 triphosphate, ST-193, and mixtures thereof. T The compounds and compositions of the present invention are also intended for use with general care provided patients with Arenaviridae viral infections, including parenteral fluids (including dextrose saline and Ringer's lactate) and nutrition, antibiotic (including Metronidazole and Cephalosporin antibiotics, such as Ceftriaxone and Cefuroxime) and/or antifungal prophylaxis, fever and pain medication, antiemetic (such as Metoclopramide) and/or antidiarrheal agents, vitamin and mineral supplements (including Vitamin C or/and K and zinc sulfate), anti-inflammatory agents (such as Ibuprofen), pain medications, and medications for other common diseases in the patient population, such anti-malarial agents (including Artemether and Artesunate-lumefantrine combination therapy), typhoid (including quinolone antibiotics, such as Ciprofloxacin, macrolide antibiotics, such as Azithromycin, cephalosporin antibiotics, such as Ceftriaxone, or aminopenicillins, such as Ampicillin), or shigellosis.

The present invention further discloses use of said compound of formula (I) or their suitable pharmaceutical compositions for the treatment of Cryopyrin Associated Periodic Syndromes (CAPS).

In another embodiment, the present invention provides a method of treating Cryopyrin Associated Periodic Syndromes (CAPS) using pharmaceutical composition of compound of formula (I) or its pharmaceutically acceptable salts. In a preferred embodiment, a method of treating Cryopyrin Associated Periodic Syndromes (CAPS) using compound of formula (I) or its pharmaceutical composition.

In a preferred embodiment, the present invention provides compound of formula (11) or its pharmaceutically acceptable salts suitable for the treatment of Cryopyrin Associated Periodic Syndromes (CAPS).

Formula (11)

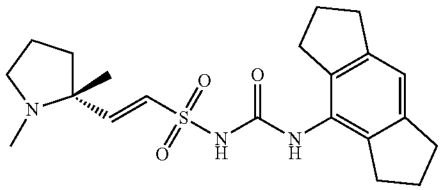

In a further preferred embodiment the present invention provides use of the compound of formula (11) or their suitable pharmaceutical compositions for the treatment of Cryopyrin Associated Periodic Syndromes (CAPS).

The method comprises administering to a subject an effective amount of a compound according to Formula (11), In another preferred embodiment, the present invention provides effective amount of compound of formula (11) or its pharmaceutically acceptable salt may be selected from 1 mg to 500 mg; preferably 1 mg to 250 mg and more preferably 1 mg to 150 mg for the treatment of Cryopyrin Associated Periodic Syndromes (CAPS).

In certain other embodiments, the compound is administered orally in an amount to provide compound of formula (11) or a pharmaceutically acceptable salt thereof in the range of about 1 mg to about 50 mg on each day the compound is administered to the subject. In certain embodiments, the compound is administered orally in an amount to provide compound of formula (11) or a pharmaceutically acceptable salt thereof in the range of about 1 mg to about 100 mg on each day the compound is administered to the subject. In certain embodiments, the compound is administered orally in an amount to provide compound of formula (11) or a pharmaceutically acceptable salt thereof in the range of about 1 mg to about 150 mg on each day the compound is administered to the subject. In certain embodiments, the compound is administered orally in an amount to provide compound of formula (11) or a pharmaceutically acceptable salt thereof in the range of about 1 mg to about 200 mg on each day the compound is administered to the subject. In certain embodiments, the compound is administered orally in an amount to provide compound of formula (11) or a pharmaceutically acceptable salt thereof in the range of about 1 mg to about 250 mg on each day the compound is administered to the subject. In certain embodiments, the compound is administered orally in an amount to provide compound of formula (11) or a pharmaceutically acceptable salt thereof in the range of about 1 mg to about 300 mg on each day the compound is administered to the subject. In certain embodiments, the compound is administered orally in an amount to provide compound of formula (11) or a pharmaceutically acceptable salt thereof in the range of about 1 mg to about 350 mg on each day the compound is administered to the subject. In certain embodiments, the compound is administered orally in an amount to provide compound of formula (11) or a pharmaceutically acceptable salt thereof in the range of about 1 mg to about 400 mg on each day the compound is administered to the subject. In certain embodiments, the compound is administered orally in an amount to provide compound of formula (11) or a pharmaceutically acceptable salt thereof in the range of about 1 mg to about 450 mg on each day the compound is administered to the subject. In certain embodiments, the compound is administered orally in an amount to provide compound of formula (11) or a pharmaceutically acceptable salt thereof in the range of about 1 mg to about 500 mg on each day the compound is administered to the subject.

In another preferred embodiment, the present invention provides effective amount of compound of formula (11) or its pharmaceutically acceptable salt may be administered by oral, topical, parenteral, intravenous or intramuscular route of administration. In a preferred embodiment, the present invention provides effective amount of formula (11) or its pharmaceutically acceptable salt is administered by oral route of administration.

The compound of formula (11) or its pharmaceutically acceptable salts may be provided to the subject daily, weekly, as prescribed by physician to the person in need thereof.

In one of the preferred embodiment, the present invention provides the combination of compound of formula (11) and their pharmaceutically acceptable salts with other suitable agents as therapeutic agent for the treatment of Cryopyrin Associated Periodic Syndromes (CAPS).

Wherein other suitable therapeutic agents may be selected from Inhibitors of interleukin-10 (e.g. Rilonacept, Canakinumab, and Anakinra); immune-suppressants (e.g., Methotrexate, Mercaptopurine, Cyclophosphamide), metabolic disorders drugs, glucocorticoids, non-steroidal anti-inflammatory drugs, Gasdermin D inhibitors (e.g., Necrosulfonamide); Cox-2 specific inhibitors, TNF-α binding proteins (e.g., Infliximab, Etanercept), Interferon-13, Interferon, Interleukin-2, antihistamines, beta-agonist, BTK inhibitors, anticolinergics, anti-cancer agents; anti-viral drugs, for example: Remdesivir, Lopinavir/Ritonavir, Favipiravir, Molnupiravir, Tamiflu; anti-malarial agents, for example: Choloroquinone, Hydroxyl Chloroquinone; or their suitable pharmaceutically acceptable salts. Further examples for use in combination with Non-Alcoholic Steato-Hepatitis (NASH) and fibrosis drugs; anticancer; antibiotics, for example Azithromycin; hormones, Aromatase inhibitors, Colchicine, Anticoagulants, antibodies, cytokines, anti-IL6 drugs; Antiparasitics; vaccines; Interferons; drug conjugates; Drugs originally developed for SARS (ACE2 protein decoy); Intravenous vitamin C; inhibitors of mitogen-activated protein kinase signaling (ex: BAY 43-9006); Syk inhibitors; mTOR inhibitors; antibodies (Rituxan); and BCR/ABL antagonist may also be used in combination with compound of formula (11) for treatment of Cryopyrin Associated Periodic Syndromes (CAPS).

In a preferred embodiment, present invention provides a pharmaceutical composition comprising compound of formula (11) or its pharmaceutically acceptable salts for treatment of Cryopyrin Associated Periodic Syndromes (CAPS).

In another preferred embodiment, the present invention provides pharmaceutical composition comprising compound of formula (11) and suitable pharmaceutically acceptable excipients for the treatment of Cryopyrin Associated Periodic Syndromes (CAPS).

The pharmaceutically acceptable excipients may be selected at least one from diluents, carriers, binders, disintegrating agents, lubricating agents, surface active agents and the like.

In another preferred embodiment, the present invention provides the pharmaceutical composition comprising compound of formula (11), its pharmaceutically acceptable salts and optionally other suitable therapeutic agents for treatment of Cryopyrin Associated Periodic Syndromes (CAPS).

Wherein other suitable therapeutic agents may be selected from Inhibitors of interleukin-1β (e.g. Rilonacept, Canakinumab, and Anakinra); immune-suppressants (e.g., Methotrexate, Mercaptopurine, Cyclophosphamide), metabolic disorders drugs, glucocorticoids, non-steroidal anti-inflammatory drugs, Gasdermin D inhibitors (e.g., Necrosulfonamide); Cox-2 specific inhibitors, TNF-α binding proteins (e.g., Infliximab, Etanercept), Interferon-13, Interferon, Interleukin-2, antihistamines, beta-agonist, BTK inhibitors, anticolinergics, anti-cancer agents; anti-viral drugs, for example: Remdesivir, Lopinavir/Ritonavir, Favipiravir, Molnupiravir, Tamiflu; anti-malarial agents, for example: Choloroquinone, Hydroxyl Chloroquinone; or their suitable pharmaceutically acceptable salts. Further examples for use in combination with Non-Alcoholic Steato-Hepatitis (NASH) and fibrosis drugs; anticancer; antibiotics, for example Azithromycin; hormones, Aromatase inhibitors, Colchicine, Anticoagulants, antibodies, cytokines, anti-IL6 drugs; Antiparasitics; vaccines; Interferons; drug conjugates; Drugs originally developed for SARS (ACE2 protein decoy); Intravenous vitamin C; inhibitors of mitogen-activated protein kinase signaling (ex: BAY 43-9006); Syk inhibitors; mTOR inhibitors; antibodies (Rituxan); and BCR/ABL antagonist may also be used in combination with compound of formula (11) for treatment of Cryopyrin Associated Periodic Syndromes (CAPS).

In an embodiment, the present invention provides a pharmaceutical composition comprising compound of formula (11) or its pharmaceutically acceptable salts wherein effective amount of compound of formula (11) or its pharmaceutically acceptable salt may be selected from 1 mg to 500 mg; preferably 1 mg to 250 mg and more preferably 1 mg to 150 mg for the treatment of Cryopyrin Associated Periodic Syndromes (CAPS).

In another embodiment, the present invention further discloses use of said compound of formula (11) or their suitable pharmaceutical compositions for the treatment of Cryopyrin Associated Periodic Syndromes (CAPS).

In another embodiment, the present invention provides use of the compound of formula (11) wherein the compound is administrated in a daily dosage range is selected from 1 mg to 500 mg, preferably selected from 1 mg to 250 mg, more preferably selected from 1 mg to 150 mg.

In another preferred embodiment, the present invention provides a method of treating Cryopyrin Associated Periodic Syndromes (CAPS) using pharmaceutical composition of compound of formula (11) or its pharmaceutically acceptable salts. In a preferred embodiment, a method of treating Cryopyrin Associated Periodic Syndromes (CAPS) using compound of formula (11) or its pharmaceutical composition.

In another preferred embodiment of the present invention provides a process for the preparation of a stable pharmaceutical composition of compounds of formula (11).

The stable pharmaceutical composition may be made by dry mixing, wet granulation or dry granulation methods by techniques known to persons skilled in the art. Thus, for example, In wet granulation process, the drug is mixed with one or more pharmaceutical excipients and granulated with suitable binding solution as described earlier, to form wet granules, the wet granules are dried and optionally sieved. The dried granules are mixed with one or more suitable excipients from those described elsewhere and then compressed into tablets or filled into capsules.

In dry mixing process, the drug is mixed with all the pharmaceutical excipients required. Theblend is mixed with one or more suitable excipients from those described elsewhere and then final blend is either compressed into tablets or filled in capsules.

In dry granulation process, the drug is mixed with one or more pharmaceutical excipients and compressed into slugs and these slugs are passed through required sieve. The sieved granules are mixed with one or more suitable excipients from those described elsewhere and then compressed into tablets or filled into capsules.

One or more solvents or vehicle used in the formulation are selected from water, acetone, chloroform, dichloromethane, ethyl alcohol, ethyl acetate, methyl alcohol, isopropyl alcohol and combinations thereof and other such materials known to those of ordinary skill in the art.

In an embodiment, the pharmaceutically acceptable excipients described in the present invention are selected at least one from diluents, carriers, binders, disintegrating agents, lubricating agents, surface active agents and the like.

Diluents include, but are not limited to lactose monohydrate, polymethacrylates selected from Eudragit, potassium chloride, sulfobutylether b-cyclodextrin, sodium chloride and spray dried lactose, combinations thereof and other such materials known to those of ordinary skill in the art.

Carriers include, but are not limited to lactose, white sugar, sodium chloride, glucose, urea, starch, calcium carbonate and kaolin, crystalline cellulose and silicic acid, combinations thereof and other such materials known to those of ordinary skill in the art.

Binders include, but are not limited to carbomers selected from carbopol, gellan, gum Arabic, hydrogenated vegetable oil, polymethacrylates selected from Eudragit, xanthan, lactose and Zein, combinations thereof and other such materials known to those of ordinary skill in the art.

Disintegrating agents include, but are not limited to, bicarbonate salt, chitin, gellan gum, polacrillin potassium and docusate sodium, combinations thereof and other such materials known to those of ordinary skill in the art.

Lubricating agents used include, but are not limited to, glycerin behenate, hydrogenated vegetable oil, sodium stearyl fumarate and myristic acid, combinations thereof and other such materials known to those of ordinary skill in the art.

Surface active agents include but are not limited to, nonionic surfactant selected from alkyl polyglucosides, cocamide DEA, cocamide MBA, cocamide TEA, decyl maltoside and octyl glucoside; anionic surfactant selected from arachnidan acid and arachidonic acid; cationic surfactant selected from cetyl trimethylammonium bromide and cetylpyridinium chloride, combinations thereof and other such materials known to those of ordinary skill in the art.

General Process for Preparation

The novel compounds of the present invention can be prepared using the reactions and techniques described below, together with conventional techniques known to those skilled in the art of organic synthesis, or variations thereon as appreciated by those skilled in the art.

The reactions can be performed in solvents appropriate to the reagents and materials employed and suitable for the transformations being affected. Preferred methods include, but not limited to those described below, where all symbols are as defined earlier unless and otherwise defined below.

The compounds of the general formula (I) can be prepared as described in schemes below along with suitable modifications/variations which are well within the scope of a person skilled in the art.

Scheme 1

Formula (I)

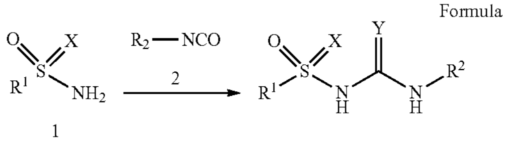

1

Wherein each of $R^1$, $R^2$, X, and Y, are as defined earlier. Compound 1 and Compound 2 can be prepared by variety of methods familiar to those skilled in art using reported procedures. Compound (1) on treatment with isocyanato derivative (2) under suitable conditions in presence of base like sodium hydride and appropriate solvent to afford compound of formula (I).

Specific reaction conditions, solvents and other parameters necessary for carrying out the process steps as described above are well within the capabilities of a person skilled in the art.

The invention is further illustrated by the following non-limiting examples which describe the preferred way of carrying out the present invention. These are provided without limiting the scope of the present invention in any way.

$^1H$ NMR spectral data given in the examples (vide infra) are recorded using a 400 MHz spectrometer (Bruker AVANCE-400) and reported in δ scale. Until and otherwise mentioned the solvent used for NMR is $CDCl_3$ using TMS as the internal standard.

Example—1

N'-cyano-N-((1,2,3,5,6,7-hexahydro-s-indacen-4-yl)carbamoyl)-5-(2-hydroxypropan-2-yl)thiophene-2-sulfonimidamide

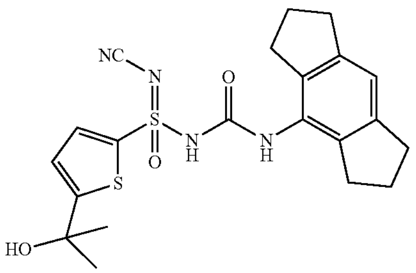 [SMILES: CC(C)(O)c1ccc(S(=O)(=NC#N)NC(=O)Nc2c3c(cc4c2CCC4)CCC3)s1]

$^1$H NMR (400 MHz, DMSO-$d_6$): δ=7.95 (bs, 1H), 7.23 (d, J=4.0 Hz, 1H), 6.82 (d, J=4.0 Hz, 1H), 6.81 (s, 1H), 5.63 (s, 2H), 2.77 (t, J=7.2 Hz, 4H), 2.68-2.65 (m, 4H), 1.94 (qui, J=7.2 Hz, 4H), 1.49 (s, 6H); MS (ESI): m/z (%)=445.10 (100%) $(M+H)^+$, 443.10 (100%) (M−H).

Example 2

N'-cyano-4-fluoro-N-((1,2,3,5,6,7-hexahydro-s-indacen-4-yl)carbamoyl)-3-(2-hydroxypropan-2-yl) benzenesulfonimidamide

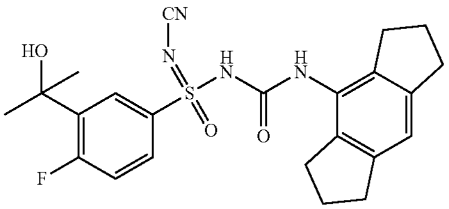 [SMILES: CC(C)(O)c1cc(S(=O)(=NC#N)NC(=O)Nc2c3c(cc4c2CCC4)CCC3)ccc1F]

$^1$H NMR (400 MHz, DMSO): δ=8.13 (dd, J=2.4 Hz, J=7.6 Hz, 1H), 8.00 (bs, 1H), 7.68-7.64 (m, 1H), 7.24-7.19 (m, 2H), 6.79 (s, 1H), 2.76-2.60 (m, 8H), 1.95-1.85 (m, 4H), 1.50 (s, 3H), 1.48 (s, 3H); MS (ESI): m/z (%)=456.88 (100%) $(M+H)^+$.

Example—3

N'-cyano-N-((1,2,3,5,6,7-hexahydro-s-indacen-4-yl) carbamoyl)-4-(2-hydroxypropan-2-yl)furan-2-sulfonimidamide

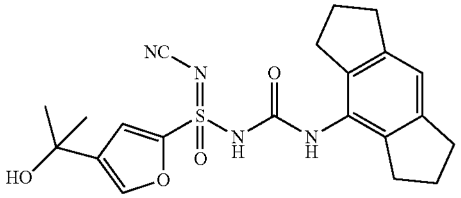 [SMILES: CC(C)(O)c1coc(S(=O)(=NC#N)NC(=O)Nc2c3c(cc4c2CCC4)CCC3)c1]

$^1$H NMR (400 MHz, DMSO-$d_6$): δ=8.10 (bs, 1H), 7.55 (s, 1H), 6.82 (s, 1H), 6.79 (s, 1H), 5.03 (s, 1H), 2.77 (t, J=7.2 Hz, 4H), 2.68 (t, J=7.2 Hz, 4H), 1.94 (qui, J=7.2 Hz, 4H), 1.38 (s, 6H); MS (ESI): m/z (%)=429.20 (100%) $(M+H)^+$, 427.30 (100%) (M−H).

Example 4

(E)-N-((1,2,3,5,6,7-hexahydro-s-indacen-4-yl)carbamoyl)-2-(thiazol-2-yl)ethenesulfonamide

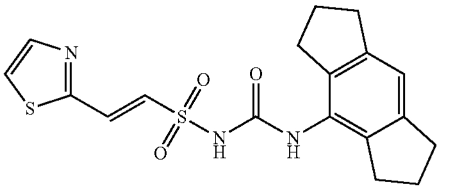 [SMILES: O=C(Nc1c2c(cc3c1CCC3)CCC2)NS(=O)(=O)/C=C/c1nccs1]

$^1$H NMR (400 MHz, DMSO-$d_6$, D20-X): δ=10.7 (br, s, 1H), 8.23 (s, 1H), 8.05 (d, J=2.8 Hz, 1H), 8.02 (d, J=2.8 Hz, 1H), 7.74 (d, J=15.2 Hz, 1H), 7.58 (d, J=15.2 Hz, 1H), 6.96 (s, 1H), 2.79 (t, J=7.2 Hz, 4H), 2.66 (t, J=6.8 Hz, 4H), 1.98-1.91 (m, 4H); MS (ESI): m/z (%)=389.92 (100%) $(M+H)^+$, 411.90 (20%) $(M+Na^+)$.

Example 5

(E)-2-(1-ethyl-1H-imidazol-2-yl)-N-((1,2,3,5,6,7-hexahydro-s-indacen-4-yl)carbamoyl)ethenesulfonamide

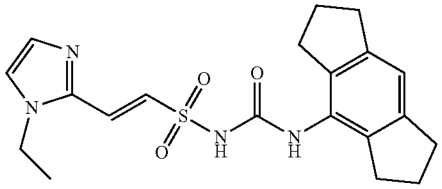 [SMILES: CCn1ccnc1/C=C/S(=O)(=O)NC(=O)Nc1c2c(cc3c1CCC3)CCC2]

$^1$H NMR (400 MHz, DMSO): δ=10.55 (bs, 1H), 8.20 (s, 1H), 7.46-7.42 (m, 2H), 7.29 (d, J=14.8 Hz, 1H), 7.13 (s, 1H), 6.95 (s, 1H), 4.16 (q, J=7.2 Hz, 2H), 2.82-2.78 (m, 4H), 2.67-2.64 (m, 4H), 1.98-1.91 (m, 4H), 4.16 (t, J=7.2 Hz, 3H); MS (ESI): m/z (%)=401.15 (100%) $(M+H)^+$; 423.15 (50%) $(M+Na)^+$.

Example 6

(E)-2-(1-ethyl-4-methyl-1H-imidazol-2-yl)-N-((1,2,3,5,6,7-hexahydro-s-indacen-4-yl)carbamoyl)ethenesulfonamide

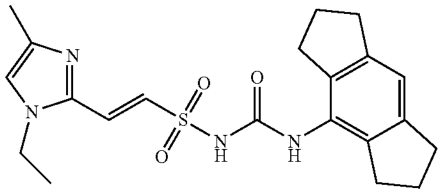 [SMILES: CCn1cc(C)nc1/C=C/S(=O)(=O)NC(=O)Nc1c2c(cc3c1CCC3)CCC2]

$^1$H NMR (400 MHz, DMSO-$d_6$): δ=10.55 (s, 1H), 8.16 (s, 1H), 7.36 (d, J=14.8 Hz, 1H), 7.21 (d, J=14.8 Hz, 1H), 7.17 (s, 1H), 6.95 (s, 1H), 4.08 (q, J=7.2 Hz, 2H), 2.80 (t, J=7.2 Hz, 4H), 2.66 (t, J=7.2 Hz, 4H), 2.12 (s, 3H), 1.98-1.91 (m, 4H), 1.27 (d, J=7.2 Hz, 3H); MS (ESI): m/z (%)=415.18 (100%) $(M+H)^+$.

Example—7

(R,E)-2-(1-ethylpyrrolidin-2-yl)-N-((1,2,3,5,6,7-hexahydro-s-indacen-4-yl)carbamoyl)-ethanesulfonamide

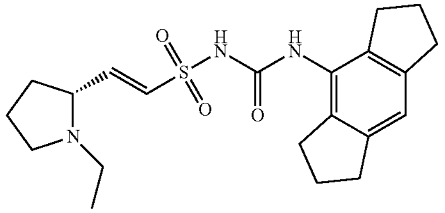 [SMILES: CCN1CCC[C@@H]1/C=C/S(=O)(=O)NC(=O)Nc1c2c(cc3c1CCC3)CCC2]

$^1$H NMR (400 MHz, DMSO-$d_6$): δ=8.03 (s, 1H), 6.92 (s, 1H), 6.87 (d, J=14.8 Hz, 1H), 6.60-6.54 (m, 1H), 3.27-3.16 (m, 3H), 2.80 (t, J=7.2 Hz, 4H), 2.67 (t, J=7.2 Hz, 4H), 2.35-2.33 (m, 2H), 2.09-1.94 (m, 6H), 1.81-1.73 (m, 2H), 1.03 (t, J=7.2 Hz, 3H); MS (ESI): m/z (%)=404.20 (100%) $(M+H)^+$.

Example—8

(R,E)-N-((1,2,3,5,6,7-hexahydro-s-indacen-4-yl)carbamoyl)-2-(pyrrolidin-2-yl)ethene-1-sulfonamide

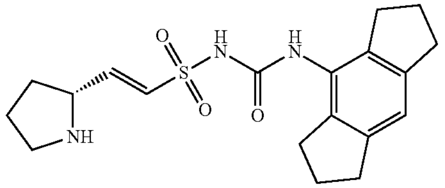 [SMILES: O=C(Nc1c2c(cc3c1CCC3)CCC2)NS(=O)(=O)/C=C/[C@H]1CCCN1]

$^1$H NMR (400 MHz, DMSO-$d_6$): δ=9.71 (brs, 1H), 7.49 (s, 1H), 6.95 (d, J=15.2 Hz, 1H), 6.80 (s, 1H), 6.36 (dd, J=7.2 Hz, J=15.2 Hz, 1H), 4.08-4.02 (m, 1H), 3.18-3.03 (m, 2H), 2.77 (t, J=7.2 Hz, 4H), 2.70 (t, J=7.2 Hz, 4H), 2.14-2.07 (m, 4H), 2.03-1.80 (m, 6H), 1.70-1.60 (m, 1H); MS (ESI): m/z (%)=376.10 (100%) $(M+H)^+$, 374.05 (100%) (M−1).

Example—9

(R,E)-N-((1,2,3,5,6,7-hexahydro-s-indacen-4-yl)carbamoyl)-2-(1-methylpyrrolidin-2-yl)ethene-1-sulfonamide

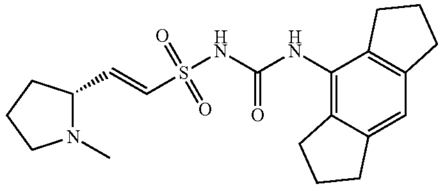 [SMILES: CN1CCC[C@@H]1/C=C/S(=O)(=O)NC(=O)Nc1c2c(cc3c1CCC3)CCC2]

$^1$H NMR (400 MHz, DMSO-$d_6$): δ=10.53 (brs, 1H), 7.97 (s, 1H), 6.92 (s, 1H), 6.84 (d, J=15.2 Hz, 1H), 6.53 (dd, J=7.6 Hz, J=15.2 Hz, 1H), 3.13-3.04 (m, 1H), 3.05-2.92 (m, 1H), 2.80 (t, J=7.2 Hz, 4H), 2.67 (t, J=7.2 Hz, 4H), 2.33-2.28 (m, 1H), 2.26 (s, 3H), 2.05-1.91 (m, 5H), 1.79-1.72 (m, 2H), 1.59-1.54 (m, 1H); MS (ESI): m/z (%)=390.17 (100%) $(M+H)^+$, 388.07 (30%) (M−1).

Example—10

(S,E)-2-(1-ethylpyrrolidin-2-yl)-N-((1,2,3,5,6,7-hexahydro-s-indacen-4-yl)carbamoyl)-ethanesulfonamide

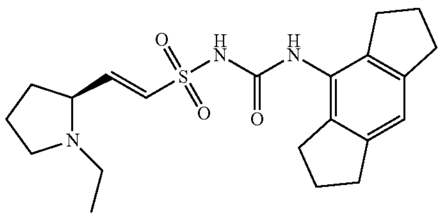 [SMILES: CCN1CCC[C@H]1/C=C/S(=O)(=O)NC(=O)Nc1c2c(cc3c1CCC3)CCC2]

$^1$H NMR (400 MHz, DMSO-$d_6$): δ=8.03 (s, 1H), 6.92 (s, 1H), 6.87 (d, J=14.8 Hz, 1H), 6.60-6.54 (m, 1H), 3.27-3.16 (m, 3H), 2.80 (t, J=7.2 Hz, 4H), 2.67 (t, J=7.2 Hz, 4H), 2.35-2.33 (m, 2H), 2.09-1.94 (m, 6H), 1.81-1.73 (m, 2H), 1.03 (t, J=7.2 Hz, 3H); MS (ESI): m/z (%)=404.20 (100%) $(M+H)^+$.

Example—11

(R,E)-2-(1,2-dimethylpyrrolidin-2-yl)-N-((1,2,3,5,6,7-hexahydro-s-indacen-4-yl)carbamoyl)ethene-1-sulfonamide

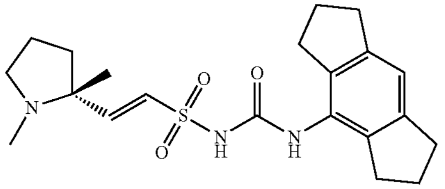 [SMILES: CN1CCC[C@]1(C)/C=C/S(=O)(=O)NC(=O)Nc1c2c(cc3c1CCC3)CCC2]

$^1$H NMR (400 MHz, DMSO-$d_6$): δ=8.04 (s, 1H), 6.93 (s, 1H), 6.74 (d, J=15.6 Hz, 1H), 6.65 (d, J=15.2 Hz, 1H), 2.93-2.86 (m, 1H), 2.80 (t, J=7.2 Hz, 4H), 2.67 (t, J=7.2 Hz, 4H), 2.19 (s, 3H), 1.99-1.91 (m, 5H), 1.80-1.69 (m, 4H), 1.13 (s, 3H), MS (ESI): m/z (%)=404.16 (100%) $(M+H)^+$.

Example—12

(S,E)-2-(1,2-dimethylpyrrolidin-2-yl)-N-((1,2,3,5,6,7-hexahydro-s-indacen-4-yl)carbamoyl)ethene-1-sulfonamide

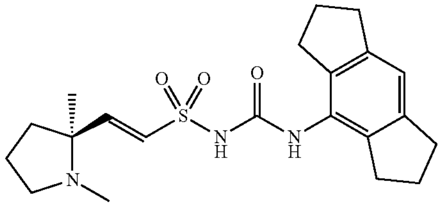 [SMILES: CN1CCC[C@@]1(C)/C=C/S(=O)(=O)NC(=O)Nc1c2c(cc3c1CCC3)CCC2]

1H NMR (400 MHz, DMSO-d6): δ=8.04 (s, 1H), 6.93 (s, 1H), 6.73 (d, J=15.2 Hz, 1H), 6.65 (d, J=15.2 Hz, 1H), 2.80 (t, J=7.2 Hz, 4H), 2.68 (t, J=7.2 Hz, 4H), 2.20 (s, 3H), 1.96 (m, 4H), 1.72 (m, 4H), 1.13 (s, 3H); MS (ESI): m/z (%)=404.25 (100%) (M+1).

Example—13

Sodium(S,E)-((2-(1,2-dimethylpyrrolidin-2-yl)vinyl)sulfonyl)((1,2,3,5,6,7-hexahydro-s-indacen-4-yl)carbamoyl)amide

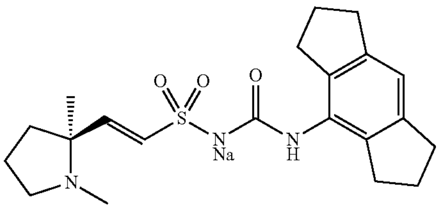

1H NMR (400 MHz, DMSO-d6): δ=7.33 (s, 1H), 6.77 (s, 1H), 6.56 (d, J=15.2 Hz, 1H), 6.16 (d, J=16 Hz, 1H), 2.76 (t, J=7.2 Hz, 4H), 2.69 (t, J=7.2 Hz, 4H), 2.62 (m, 1H), 2.08 (s, 3H), 1.90 (m, 4H), 1.72 (m, 4H), 1.60 (m, 3H), 1.01 (s, 3H); MS (ESI): m/z (%)=404.20 (100%) (M+1).

Example—14

Potassium (R,E)-((2-(1,2-dimethylpyrrolidin-2-yl)vinyl)sulfonyl)((1,2,3,5,6,7-hexahydro-s-indacen-4-yl)carbamoyl)amide

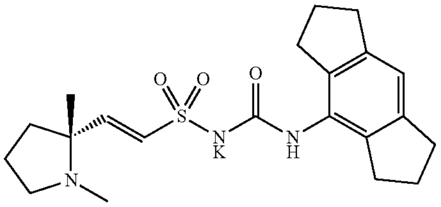

$^1$H NMR (400 MHz, DMSO-$d_6$): δ=7.33 (s, 1H), 6.77 (s, 1H), 6.58 (d, J=15.6 Hz, 1H), 6.18 (d, J=15.6 Hz, 1H), 2.77-2.72 (m, 5H), 2.69 (t, J=7.2 Hz, 4H), 2.64-2.58 (m, 1H), 2.08 (s, 3H), 1.90 (quin, J=7.6 Hz, 4H), 1.75-1.70 (m, 3H), 1.62-1.60 (m, 1H), 1.01 (s, 3H); MS (ESI): m/z (%)=404.21 (100%) $(M-K)^+$.

Example—15

Sodium(R,E)-((2-(1,2-dimethylpyrrolidin-2-yl)vinyl)sulfonyl)((1,2,3,5,6,7-hexahydro-s-indacen-4-yl)carbamoyl)amide

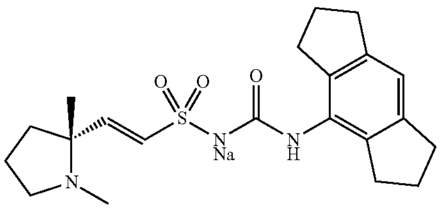

$^1$H NMR (400 MHz, DMSO-$d_6$): δ=7.36 (s, 1H), 6.77 (s, 1H), 6.57 (d, J=15.6 Hz, 1H), 6.19 (d, J=15.6 Hz, 1H), 2.76 (t, J=7.2 Hz, 5H), 2.69 (t, J=7.2 Hz, 4H), 2.64-2.59 (m, 1H), 2.08 (s, 3H), 1.91 (quin, J=7.6 Hz, 4H), 1.74-1.68 (m, 3H), 1.62-1.60 (m, 1H), 1.01 (s, 3H); MS (ESI): m/z (%)=404.17 (100%) $(M-Na)^+$.

Example—16

(E)-N'-cyano-2-((S)-1,2-dimethylpyrrolidin-2-yl)-N-((1,2,3,5,6,7-hexahydro-s-indacen-4-yl)carbamoyl)ethene-1-sulfonimidamide

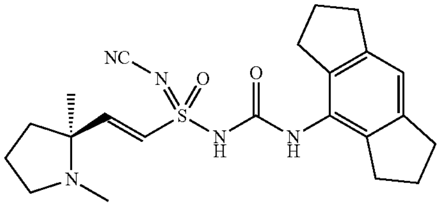 [SMILES: CN1CCC[C@@]1(C)/C=C/S(=O)(=NC#N)NC(=O)Nc1c2c(cc3c1CCC3)CCC2]

$^1$H NMR (400 MHz, DMSO-$d_6$): δ=9.94 (s, 1H), 8.06 (s, 1H), 6.97 (d, J=16.0 Hz, 1H), 6.83 (s, 1H), 6.56-6.48 (m, 1H), 3.58 (br s, 1H), 3.24-3.12 (m, 1H), 2.77 (t, J=7.2 Hz, 4H), 2.69 (t, J=7.2 Hz, 7H), 2.10-1.99 (m, 3H), 1.95-1.88 (m, 5H), 1.53-1.36 (m, 3H); ESI-Q-TOF-MS: m/z $[M-HCl+H]^+$ calcd for $[C22H30N5O2S]^+$: 428.2120; found: 428.2052

Example—17

(E)-N'-cyano-N-((1,2,3,5,6,7-hexahydro-s-indacen-4-yl)carbamoyl)-2-((R)-1-methylpyrrolidin-2-yl)ethene-1-sulfonimidamide

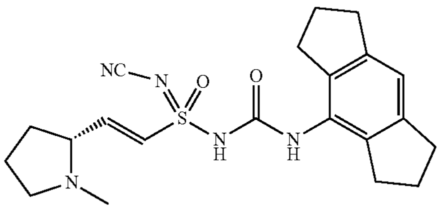 [SMILES: CN1CCC[C@@H]1/C=C/S(=O)(=NC#N)NC(=O)Nc1c2c(cc3c1CCC3)CCC2]

$^1$H NMR (400 MHz, DMSO-$d_6$): δ=9.82 (s, 1H), 8.06 (s, 1H), 7.11-7.02 (m, 1H), 6.83 (s, 1H), 6.43-6.35 (m, 1H), 4.99 (br s, 1H), 3.62-3.61 (m, 1H), 3.09-3.07 (m, 1H), 2.77 (t, J=7.2 Hz, 7H), 2.70 (t, J=7.2 Hz, 4H), 2.33-2.27 (m, 1H), 2. 1-1.88 (m, 7H); MS (TOF): m/z (%)=414.1897 (100%) $(M+H)^+$, 412.1765 (100%) $(M-1)^-$.

Example—18

(E)-N'-cyano-2-((R)-1,2-dimethylpyrrolidin-2-yl)-N-((1,2,3,5,6,7-hexahydro-s-indacen-4-yl)carbamoyl) ethene-1-sulfonimidamide

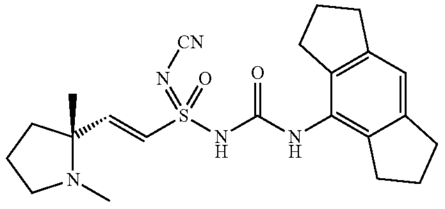

$^1$H NMR (400 MHz, DMSO-$d_6$): δ=9.98 (s, 1H), 8.03 (s, 1H), 6.94-6.90 (m, 1H), 6.83 (s, 1H), 6.54-6.51 (m, 1H), 2.77 (t, J=7.2 Hz, 5H), 2.70 (t, J=7.2 Hz, 5H), 2.62 (br s, 3H), 1.99-1.90 (br s, 2H), 1.97-1.93 (m, 6H), 1.48-1.46 (m, 3H); MS (TOF): m/z (%)=428.2097 (100%) $(M+H)^+$, 426.1941 (60%) $(M-1)^-$.

Example—19

N-((1,2,3,5,6,7-hexahydro-s-indacen-4-yl)carbamoyl)-1-((1S,8aR)-3,3,8a-trimethyloctahydropyrrolo[1,2-a]pyrazin-1-yl)methanesulfonamide

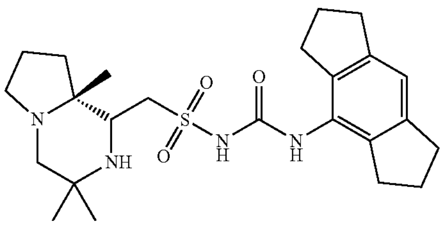

$^1$H NMR (400 MHz, DMSO-$d_6$): δ=7.92 (s, 1H), 6.87 (s, 1H), 3.42-3.26 (m, 5H), 3.07-3.01 (m, 1H), 2.89-2.80 (m, 1H), 2.89-2.80 (m, 1H), 2.77 (t, J=7.2 Hz, 4H), 2.73-2.67 (m, 4H), 2.58-2.44 (m, 1H), 2.38-2.33 (m, 1H), 1.98-1.92 (m, 4H), 1.69-1.61 (m, 2H), 1.31 (s, 3H), 1.18 (s, 3H), 0.78 (s, 3H); MS (TOF): m/z (%)=461.2537 (100%) $(M+H)^+$.

Example—20

N-((1,2,3,5,6,7-hexahydro-s-indacen-4-yl)carbamoyl)-1-((4S,8aS)-2,3,3,8a-tetramethyloctahydropyrrolo[1,2-a]pyrazin-4-yl)methanesulfonamide

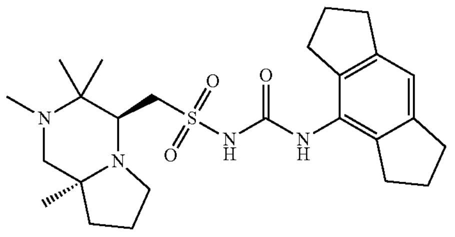 [SMILES: CN1C[C@]2(C)CCCN2[C@H](CS(=O)(=O)NC(=O)Nc2c3c(cc4c2CCC4)CCC3)C1(C)C]

$^1$H NMR (400 MHz, DMSO-$d_6$): δ=8.03 (s, 1H), 6.93 (s, 1H), 3.52-3.48 (m, 2H), 3.18-3.09 (m, 1H), 3.09-3.01 (m, 1H), 3.00-2.88 (m, 1H), 2.81 (t, J=7.2 Hz, 4H), 2.70 (t, J=7.2 Hz, 4H), 2.36-2.33 (m, 2H), 2.19 (s, 3H), 2.01-1.93 (m, 4H), 1.76-1.69 (m, 1H), 1.67-1.54 (m, 3H), 1.01-1.04 (m, 6H), 0.86 (s, 3H); MS (TOF): m/z (%)=475.2709 (100%) $(M+H)^+$, 473.2593 (20%) (M−1).

Example—21

(E)-3-(dimethylamino)-N-((1,2,3,5,6,7-hexahydro-s-indacen-4-yl)carbamoyl)prop-1-ene-1-sulfonamide

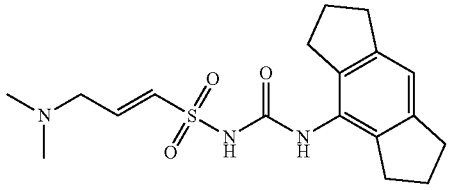 [SMILES: CN(C)C/C=C/S(=O)(=O)NC(=O)Nc1c2c(cc3c1CCC3)CCC2]

$^1$H NMR (400 MHz, DMSO-$d_6$): δ=10.22 (brs, 1H), 7.94 (s, 1H), 6.91 (s, 1H), 6.86 (d, J=15.2 Hz, 1H), 6.62-6.55 (m, 1H), 3.27 (t, J=6.0 Hz, 2H), 2.79 (t, J=7.2 Hz, 4H), 2.67 (t, J=7.2 Hz, 4H), 2.30 (s, 6H), 1.99-1.91 (m, 4H); MS (ESI): m/z (%)=364.1513 (100%) $(M+H)^+$.

Example—22

Sodium (E)-((3-(dimethylamino)-3-methylbut-1-en-1-yl)sulfonyl)((1,2,3,5,6,7-hexahydro-s-indacen-4-yl)carbamoyl)amide

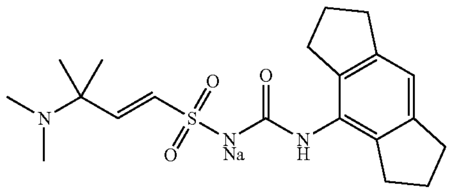

$^1$H NMR (400 MHz, DMSO-$d_6$): δ=7.36 (s, 1H), 6.77 (s, 1H), 6.51 (d, J=15.6 Hz, 1H), 6.23 (d, J=15.6 Hz, 1H), 2.76 (t, J=7.2 Hz, 4H), 2.69 (t, J=7.2 Hz, 4H), 2.11 (s, 1H), 1.94-1.87 (m, 4H), 1.06 (s, 6H); MS (TOF): m/z (%)=392.1987 (100%) $(M+H)^+$, 390.1841 (20%) (M−1).

Example—23

(S,E)-N-((1,2,3,5,6,7-hexahydro-s-indacen-4-yl)carbamoyl)-2-(2-methyl-1-(methyl-d)pyrrolidin-2-yl)ethene-1-sulfonamide

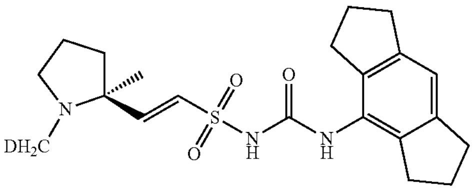

$^1$H NMR (400 MHz, DMSO-$d_6$): δ=7.93 (s, 1H), 6.91 (s, 1H), 6.71 (d, J=15.2 Hz, 1H), 6.60 (d, J=15.6 Hz, 1H), 2.85-2.83 (m, 1H), 2.80 (t, J=7.2 Hz, 4H), 2.73-2.71 (m, 1H), 2.67 (t, J=7.2 Hz, 4H), 2.15 (s, 2H), 1.95 (quin, J=7.2 Hz, 4H), 1.81-1.69 (m, 4H), 1.10 (s, 3H). ESI-Q-TOF-MS: m/z 405.2268 (100%) $[M+H]^+$, 403.1901 (100%) $[M-H]^-$.

Example—24

(R,E)-N-((1,2,3,5,6,7-hexahydro-s-indacen-4-yl)carbamoyl)-2-(2-methyl-1-(methyl-d)pyrrolidin-2-yl)ethene-1-sulfonamide

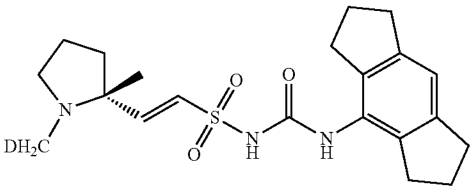

$^1$H NMR (400 MHz, DMSO-$d_6$): δ=7.94 (s, 1H), 6.91 (s, 1H), 6.72 (d, J=15.2 Hz, 1H), 6.61 (d, J=15.2 Hz, 1H), 2.88-2.83 (m, 1H), 2.80 (t, J=7.2 Hz, 4H), 2.75-2.71 (m, 1H), 2.67 (t, J=7.2 Hz, 4H), 2.15 (s, 2H), 1.95 (quin, J=7.2 Hz, 4H), 1.82-1.69 (m, 4H), 1.11 (s, 3H), ESI-Q-TOF-MS: m/z 405.2104 (100%) $[M+H]^+$, 403.1915 (100%) $[M-H]^-$.

Example—25

(R,E)-N-((1,2,3,5,6,7-hexahydro-s-indacen-4-yl)carbamoyl)-2-(1-(methyl-d)pyrrolidin-2-yl)ethene-1-sulfonamide

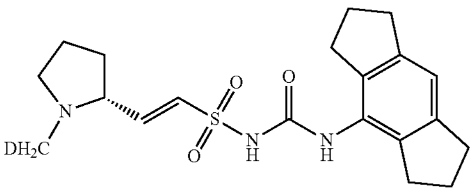

$^1$H NMR (400 MHz, DMSO-$d_6$): δ=10.5 (br s, 1H), 7.99 (s, 1H), 6.92 (s, 1H), 6.86 (d, J=15.2 Hz, 1H), 6.56 (dd, $J_1$=7.6 Hz, $J_2$=15.2 Hz, 1H), 3.12-3.06 (m, 2H), 2.80 (t, J=7.2 Hz, 4H), 2.67 (t, J=7.2 Hz, 4H), 2.38-2.32 (m, 1H), 2.25 (s, 2H), 2.08-2.01 (m, 1H), 1.95 (quin, J=7.2 Hz, 4H), 1.80-1.73 (m, 2H), 1.63-1.54 (m, 1H), ESI-Q-TOF-MS: m/z 391.1956 (100%) $[M+H]^+$, 389.1756 (100%) $[M-H]^-$.

In Vitro Study to Evaluate the Potency in Healthy Volunteers and Against CAPS Mutations:

Compound 11, a potent NLRP3 inflammazome inhibitor blocks the IL-1β and IL-18 secretion from activated THP-1 cells, hPBMCs (Human peripheral blood mononuclear cell) and whole blood treated with LPS (lipopolysaccharide) and ATP (Adenosine triphosphate). For the whole blood assay, human peripheral venous blood was collected from healthy volunteers following the protocol approved by ethics committee. Whole blood was distributed in 96-well plates and primed with LPS (500 ng/mL) for 4 hours. Different concentrations of compound 11 was added in the presence of serum free media. NLRP3 inflammasome was induced with ATP (5 mM) for 1 hour. The supernatant was collected at the end of 1 hour and assayed for released IL-1β using the ELISA method. The inhibition in the cytokine levels was plotted and the half maximal inhibitory concentration was derived.

TABLE 1

Half maximal inhibitory concentration of Compound 11 against NLRP3 mediated IL-1β release in PBMCs from healthy volunteers

| Whole Blood assay (Normal volunteer) | $IC_{50}$ (nM) Mean ± SD* |
|---|---|
| Compound 11 | 186 ± 32 |

*Mean data from three healthy volunteers

Ex-Vivo Pharmacodynamics Evaluation

In the ex-vivo pharmacodynamics evaluation, the blood was withdrawn at specific intervals after dosing and NLRP3 was induced using LPS and ATP. Inhibition of IL-1β secretion was observed over 90% with all the doses tested in SAD and MAD studies. An $ED_{90}$ was achieved below 400 ng/mL.

To examine the efficacy of Compound 11 in CAPS condition, initially the potency of Compound 11 was tested against different CAPS mutations. Human PBMCs containing monocytes express NLRP3 when induced with LPS and ATP in normal volunteers or only with LPS in CAPS patient volunteers. Human peripheral blood mononuclear cell (hPBMC) was isolated from volunteer using gradient method. hPBMC was suspended in complete growth medium and plated overnight before activating with LPS and/or ATP. Half maximal inhibitory concentrations were derived for Compound 11 against normal volunteer and CAPS patient PBMCs activated with respective stimulants and subsequent treatment with Compound 11. Compound 11 showed $IC_{50}$ of 3.0-6.0 nM in PBMCs isolated from healthy volunteers. When tested in 5 different CAPS patient volunteer PBMCs, Compound 11 showed potency between 2.2 nM and 31.3 nM. Interestingly the potency of Compound 11 was superior to the published report of MCC950, a competitor molecule where the potency was lower in similar family of mutations. Head to head in a A439V mutation, while Compound 11 was 15.1 and 31.3 nM, MCC950 showed $IC_{50}$≥100 nM. (Wellcome Open Research 2020, 5:247)

TABLE 2

| Half maximal inhibitory concentration of Compound 11 against NLRP3 mediated IL-1β release in PBMCs from healthy and CAPS volunteers | | | | | | |
|---|---|---|---|---|---|---|
| Compound 11 | Healthy Volunteers | CAPS patient Volunteers | | | | |
| NLRP3 Mutation | WT (Wild Type) | A441V | E692K | A439V | A441V | A439V |
| $IC_{50}$ | 3.0-6.0 nM* | 2.7 nM | 2.2 nM | 15.1 nM | 30.3 nM | 31.3 nM |

*PBMCs from normal volunteers (NLRP3 WT) were challenged with 10 ng LPS and 5 mM ATP to activate the inflammasome complex and secreted IL-1β was measured. PBMCs from CAPS patient volunteers (NLRP3 mutant) were challenged with 100 ng LPS to activate the inflammasome complex and secreted IL-1β was measured.

In a phase 1 single ascending dose clinical study, Compound 11 showed a good pharmacokinetic profile with dose dependent modulation in the plasma levels of healthy volunteers. In the multiple ascending BID study too, Compound 11 achieved steady state levels dose dependently.

In conclusion, Compound 11 had shown nM potency in NLRP3 mediated IL-1β inhibition in preclinical studies and studies involving human healthy patients with wild type NLRP3, also showed a perfect translation in the clinic. Interestingly, it turned out to be equally potent in NLRP3 mediated IL-1β inhibition in proven CAPS patients with defined gain of function mutation of NLRP3

Efficacy of Compound 11 in Healthy Adult Human Subjects:

Protocol Title: A Phase 1, Prospective study of the compound 11 administered via oral route to investigate the safety, tolerability, pharmacokinetics and pharmacodynamics in Healthy Adult Human Subjects.

Objectives:

Primary Objective:

- To evaluate safety and tolerability of the compound 11 administered to healthy subjects.

Secondary Objective(s):

- To characterize the pharmacokinetics of the compound 11 when administered as a single oral dose to healthy subjects.
- To evaluate pharmacodynamic properties of the compound 11 in healthy subjects.

Exploratory(s):

- To profile and identify/quantify unique metabolite(s) of the compound 11 in plasma and urine.
- To evaluate any other pharmacodynamic properties of the compound 11 in healthy subjects.

Criteria for Safety:

- Recording of vital signs like body temperature, blood pressure, Respiratory rate, $SpO_2$ and radial pulse.
- Clinical examinations, which include general examination as well as systemic examination (cardiovascular system (CVS), respiratory system (RS), gastrointestinal system (GI), central nervous system (CNS))
- ECG evaluation
- Clinical laboratory tests (i.e. hematology, serum biochemistry, urinalysis, and serology)
- Frequency and severity of adverse events (AEs) for all subjects enrolled are recorded.
- All AEs, are classified using
  - causality
  - severity
  - seriousness Methodology:

It is an open label, study designed to evaluate safety, tolerability, pharmacokinetics (PK) and pharmacodynamics (PD) following a single-oral dose administration of the compound 11 to healthy subjects.

In this study each cohort containing six subjects, given a single oral dose of the compound 11 in ascending manner. Initially, up to 3 cohorts (comprising of 25 mg, 50 mg and 100 mg dose) of 18 subjects will be enrolled and dosed. Interim analysis is done after completion of three cohorts and submitted to Central Licensing Authority.

Duration of the treatment: single dose

Subjects were eligible for inclusion into the study if they were healthy, aged 18 through 55 years (both inclusive), had a body mass index (BMI) between 18.5 and 30.0 kg/m2 (both inclusive) with a body weight of 50 to 100 kg (both inclusive), had normal QTc interval [QTcF≤450 ms] at screening and check-in, agreed to comply with trial procedures and willing to practice highly effective contraception.

Subjects were excluded from the study if they have history or presence of systemic disorders/disease within the past 3 months; history of clinically significant hypersensitivity, intolerance, or allergies; history of COVID-19 infection within 14 days or contact with a confirmed active COVID-19 positive patient within 14 days; or positive COVID-19 test within 5 days of check-in; subjects who had systolic blood pressure more than 140 mmHg or less than 100 mmHg or diastolic blood pressure more than 90 mmHg or less than 60 mmHg; Pulse rate less than 55/minute or more than 100/minute and other exclusion criteria as defined in protocol.

Such subjects are invited to participate in this study.

Evaluation for safety and efficacy is done as per the activity chart.

No. of subjects in treatment arm: A total of 18 subjects i.e. 06 subject in each cohort S1 (25 mg), cohort S2 (50 mg) and cohort S3 (100 mg) were enrolled. A total of 18 subjects were enrolled and dosed with the compound capsule. A total of 17 subjects completed the study.

Duration of treatment: Subjects were enrolled within 28 day screening period, received single doses of the compound 11 capsule orally and followed up for upto 48 hours post dose

Results

Of 18 enrolled subjects, 17 subjects completed the study. All 18 subjects were Asian, Male subjects. Overall, for this study the mean (range) age was 37 years (23 to 47 years) and BMI was 23.51 kg/m2 (19.71 to 28.01 kg/m2. The compound administered via oral route was found to be safe and well tolerated till 100 mg single dose in healthy subjects. No subjects were discontinued from the study because of adverse events.

Pharmacokinetic and Pharmacokinetic Results

Pharmacokinetic Results

The plasma and urine samples were analyzed for estimation of the compound using a separately validated LC-MS/MS assays. The concentration-time data were subjected for evaluation of pharmacokinetic parameters.

Cohort S1 (25 mg Dose)

A total 06 healthy male subjects received 25 mg dose of the compound 11.

Note: 01 subject in cohort S1 withdrawn his consent and discontinued from the study. Hence, this subject was not used for pharmacokinetic assessment.

Pharmacokinetic evaluation indicated that the drug was well absorbed on oral administration, with median time to reach maximal plasma concentration, median Tmax is at 1.500 hr ranging from 0.500 hrs to 2.000 hrs. The mean elimination half-life was 6.526±0.67 hrs. The mean Cmax and AUC0-t were 3.393±0.72 μg/mL and 26.967±0.39 hr*μg/mL, respectively. The mean plasma clearance was 0.922±0.01 L/hr and mean volume of distribution was 8681.147±929.14 mL. Mean cumulative percentage urinary recovery of an unchanged the compound was 93.26%.

Cohort S2 (50 mg Dose)

A total 06 healthy male subjects received 50 mg dose of the compound 11.

Pharmacokinetic evaluation indicated that the drug was well absorbed on oral administration, with median time to reach maximal plasma concentration, median Tmax is at 1.000 hr ranging from 0.500 hrs to 2.000 hrs. The mean elimination half-life was 5.818±0.47 hrs. The mean Cmax and AUC0-t were 5.724±0.52 μg/mL and 40.838±7.20 hr*μg/mL, respectively. The mean plasma clearance was 1.238±0.22 L/hr and mean volume of distribution was 10285.52±1174.32 mL. Mean cumulative percentage urinary recovery of an unchanged the compound was 69.09%.

Cohort S3 (100 mg Dose)

A total 06 healthy male subjects received 100 mg dose of the compound 11

Pharmacokinetic evaluation indicated that the drug was well absorbed on oral administration, with median time to reach maximal plasma concentration, median Tmax is at 1.000 hr ranging from 0.500 hrs to 1.500 hrs. The mean elimination half-life was 6.275±0.65 hrs. The mean Cmax and AUC0-t were 11.489±1.01 μg/mL and 92.302±14.90 hr*μg/mL, respectively. The mean plasma clearance was 1.099±0.15 L/hr and mean volume of distribution was 9847.576±825.72 mL. Mean cumulative percentage urinary recovery of an unchanged the compound was 76.63%.

Overall, the compound 11 exhibited rapid oral absorption from gastrointestinal track with maximum concentration achieved at 1.0 to 1.5 hours. Dose-related increase in exposure (Cmax & AUC) of the compound 11 was observed from 25 to 100 mg dose. The mean elimination half-life was about 6.0-6.5 h across all three doses. The majority of an unchanged the compound 11 was recovered in urine suggests that the renal is a primary route of the compound excretion.

Pharmacodynamic Results

Blood isolated at predose, 3, 6, 12 and 24 hours was activated ex vivo with LPS and ATP and secreted IL-1β and IL18 was measured in LPS/ATP treated and untreated whole blood.

Descriptive statistics (n, mean, standard deviation) of the corrected IL-1β whole blood concentration was summarized by treatment and time point. Levels of BLQ were set to 0.

Corrected IL-1β whole blood concentration was derived as: (IL-1β concentration in treated sample−IL-1β concentration in untreated sample).

Percentage of IL-1β inhibition is calculated as: [(treated concentration at predose−untreated concentration at predose)−(treated concentration at Rx time point−untreated concentration at Rx time point)]/(treated concentration at predose−untreated concentration at predose)*100%.

All 17 subjects showed more than 90% inhibition of IL-1β after the administration of compound 11. Single dose of 25 mg, 50 mg & 100 mg, the compound 11 showed ex vivo IL-1β inhibition above 90% till 6 hrs, 12 hours & 24 hrs post dose, respectively.

We claim:

1. A method for the treatment of Cryopyrin Associated Periodic Syndromes (CAPS), which comprises administering a compound of formula (11)

Formula (11)

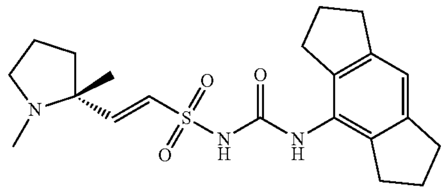

or its pharmaceutically acceptable salts.

2. The method as claimed in claim 1, wherein therapeutically effective amount of compound of formula (11) or its pharmaceutically acceptable salt is selected from 1 mg to 500 mg.

3. The method as claimed in claim 1, wherein compound of formula (11) or its pharmaceutically acceptable salt is administered by oral, topical or parenteral route of administration.

4. The method as claimed in claim 1, wherein compound of formula (11) or its pharmaceutically acceptable salt is administered in combination with other suitable therapeutic agents.

5. The method as claimed in claim 1, wherein compound of formula (11) or its pharmaceutically acceptable salt is administered in the form of pharmaceutical composition.

* * * * *